US012782339B2

(12) United States Patent
Lamar et al.

(10) Patent No.: US 12,782,339 B2
(45) Date of Patent: Nov. 3, 2026

(54) SYNTHESIS AND USE OF N-BENZYL SULFONAMIDES

(71) Applicant: THE UNIVERSITY OF TULSA, Tulsa, OK (US)

(72) Inventors: Angus A Lamar, Tulsa, OK (US); Robert J Sheaff, Owasso, OK (US)

(73) Assignee: THE UNIVERSITY OF TULSA, Tulsa, OK (US)

( * ) Notice: Subject to any disclaimer, the term of this patent is extended or adjusted under 35 U.S.C. 154(b) by 741 days.

(21) Appl. No.: 18/017,534

(22) PCT Filed: Jul. 23, 2021

(86) PCT No.: PCT/US2021/043012
§ 371 (c)(1),
(2) Date: Jan. 23, 2023

(87) PCT Pub. No.: WO2022/020742
PCT Pub. Date: Jan. 27, 2022

(65) Prior Publication Data
US 2023/0266302 A1 Aug. 24, 2023

Related U.S. Application Data

(60) Provisional application No. 63/056,211, filed on Jul. 24, 2020.

(51) Int. Cl.

| | |
|---|---|
| ***A61K 31/352*** | (2006.01) |
| ***A61K 31/415*** | (2006.01) |
| ***C07D 265/38*** | (2006.01) |
| ***G01N 21/76*** | (2006.01) |
| ***G01N 33/50*** | (2006.01) |
| ***G01N 33/573*** | (2006.01) |

(52) U.S. Cl.
CPC ....... *G01N 33/5014* (2013.01); *A61K 31/352* (2013.01); *A61K 31/415* (2013.01); *C07D 265/38* (2013.01); *G01N 21/763* (2013.01); *G01N 33/5735* (2013.01)

(58) Field of Classification Search
CPC ........................................................ A61K 31/352
See application file for complete search history.

(56) References Cited

U.S. PATENT DOCUMENTS

| | | | |
|---|---|---|---|
| 6,558,916 | B2 | 5/2003 | Veerapandian et al. |
| 7,083,911 | B2 | 8/2006 | Wood et al. |
| 7,282,348 | B2 | 10/2007 | Riss et al. |
| 7,338,778 | B2 | 3/2008 | Pitner et al. |
| 7,741,067 | B2 | 6/2010 | Hawkins et al. |

(Continued)

OTHER PUBLICATIONS

Abebe (Screening of Heteroaromatic N-Benzyl Sulfonamides for Novel Chemotherapeutic Drugs,âThe University of TulsaâProQuest Dissertations & Theses, 2019.â27665704). (Year: 2019).*

(Continued)

*Primary Examiner* — Benjamin J Packard
(74) *Attorney, Agent, or Firm* — McAFee & Taft

(57) ABSTRACT

Disclosed is a method for preparing N-benzyl sulfonamides. Also disclosed is a composition for treating cancer. The composition includes a N-benzyl sulfonamide and a metabolic inhibitor. Also disclosed is a method for determining the impact on cell ATP levels of a composition containing a N-benzyl sulfonamide with or without a metabolic inhibitor.

17 Claims, 22 Drawing Sheets

(56) References Cited

U.S. PATENT DOCUMENTS

| | | | |
|---|---|---|---|
| 7,875,605 B2 | 1/2011 | Ramakrishna et al. | |
| 8,802,411 B2 | 8/2014 | Zegzouti et al. | |
| 9,422,235 B2 | 8/2016 | Yacovan et al. | |
| 2008/0005762 A1 | 1/2008 | Seko | |
| 2008/0161187 A1 | 7/2008 | Grammenos et al. | |
| 2008/0206798 A1 | 8/2008 | Wood et al. | |
| 2012/0258480 A1 | 10/2012 | Zegzouti et al. | |
| 2013/0252270 A1* | 9/2013 | McKim | G01N 33/502<br>435/29 |

OTHER PUBLICATIONS

Hopkins et al (Org. Biomol. Chem, vol. 17, (2019), pp. 8391 to 8402). (Year: 2019).*

European Search Report for European Patent Application No. 21845773.7; Aug. 9, 2024; pp. 1-9.

Promego Safety Data Sheet; Celltiter-Glo Luminescent Cell Via. Assay; G7570 Jul. 23, 2020.

Ben Schmidt; Why You Don't Need to Select a Wavelingth for a Luciferase Assay; Promega Connections; Jun. 7, 2019.

Promega Technical Bulletin; Celltiter-Glo Luminescent Cell Viability Assay; Mar. 2015.

Promega Technical Bulletin; Celltiter-Blue Cell Viability Assay; Mar. 2016.

Robert T. Dorr et al.; Characterization of a Membrane-Active Anti-Tumor Agent, UA8967; Invest New Drugs; Nov. 23, 2012.

* cited by examiner 43 44 45

46 47 48

49 50 51

52 53 54

112 113 114 115 116 117 118 119 120 121 122 123

124

127

130

125

128

131

126

129

132

133

134

135

136

137

138

139

POC (Percent of DMSO Control) of various cell lines

| Compound | HDF | H293 | PC3 | BxPC3 | HeLa | NCI-H196 | DMS-114 | MCF10A | MCF7 | T47D | SkBr3 | MDA-MB |
|---|---|---|---|---|---|---|---|---|---|---|---|---|
| **2** | 57.7 | 32.9 | 65.1 | 45.6 | 64.3 | 48.8 | 84.3 | 46.5 | 40.8 | 60.9 | 45.8 | 50.6 |
| **5** | 42.1 | 33.5 | 75.1 | 47.7 | 25.1 | 18.2 | 51.0 | 25.1 | 48.2 | 69.2 | 40.2 | 53.6 |
| **6** | 42.2 | 23.3 | 49.1 | 51.4 | 42.2 | 12.4 | 72.2 | 27.2 | 55.2 | 51.3 | 43.6 | 43.9 |
| **7** | 69.3 | 50.2 | 65.2 | 67.3 | 82.4 | 56.5 | 81.1 | 80.2 | 65.4 | 91.0 | 60.4 | 55.6 |
| **8** | 78.1 | 66.1 | 74.9 | 81.8 | 89.1 | 70.1 | 82.0 | 112.5 | 87.4 | 91.2 | 75.1 | 72.1 |
| **9** | 76.7 | 68.7 | 79.9 | 69.7 | 87.9 | 80.8 | 87.9 | 99.8 | 69.3 | 88.4 | 60.2 | 68.2 |
| **11** | 90.8 | 87.7 | 87.3 | 85.2 | 95.3 | 73.7 | 94.6 | 116.7 | 95.5 | 95.1 | 87.1 | 72.7 |
| **12** | 82.5 | 66.9 | 69.3 | 52.4 | 84.8 | 70.7 | 77.2 | 120.6 | 69.6 | 85.5 | 65.0 | 58.1 |
| **14** | 91.2 | 91.7 | 85.5 | 72.4 | 94.5 | 77.1 | 85.9 | 126.5 | 88.5 | 93.7 | 88.4 | 65.6 |
| **16** | 87.6 | 82.2 | 77.9 | 66.7 | 90.1 | 78.9 | 91.9 | 138.5 | 82.3 | 92.6 | 77.0 | 58.8 |
| **18** | 94.8 | 93.7 | 77.2 | 61.6 | 103.3 | 85.0 | 86.8 | 122.2 | 86.9 | 90.7 | 77.7 | 59.6 |
| **19** | 88.9 | 81.5 | 66.4 | 57.2 | 87.5 | 83.5 | 84.4 | 130.4 | 83.0 | 88.1 | 75.8 | 54.6 |
| **20** | 94.9 | 94.6 | 82.6 | 54.8 | 89.2 | 82.2 | 76.4 | 119.6 | 81.0 | 88.0 | 71.4 | 55.9 |
| **21** | 98.5 | 99.2 | 68.3 | 60.3 | 102 | 87.7 | 87.1 | 121.9 | 90.5 | 89.6 | 82.7 | 68.5 |
| **22** | 54.2 | 61.4 | 79.1 | 77.4 | 77.7 | 73.6 | 69.4 | 83.4 | 68.3 | 62.8 | 76.5 | 79.5 |

FIG. 9

| Entry | $R^1$ | $R^2$ | $R^3$ | $R^4$ | Compound | % Yld[a] | IC$_{50}$ (μM)[b] H293 | HeLa | NCI-H196 |
|---|---|---|---|---|---|---|---|---|---|
| 1 | H | H | Ac | 4-ClC$_6$H$_4$ | **4** | 64 | | | |
| 2 | H | H | CH$_3$ | 4-ClC$_6$H$_4$ | **29** | 32 | | | |
| 3 | H | H | H | 4-ClC$_6$H$_4$ | **2** | 60 | 56.9 | 83.2 | 57.3 |
| 4 | Br | H | H | 4-CH$_3$C$_6$H$_4$ | **5** | 34 | 60.5 | 67.3 | 44.5 |
| 5 | H | CH$_3$ | H | 4-CH$_3$C$_6$H$_4$ | **6** | 58 | 50.5 | 60.6 | 47.3 |
| 6 | CH$_3$ | H | H | C$_6$H$_5$ | **7** | 63 | 95.6 | 96.3 | 95.9 |
| 7 | CH$_3$ | H | H | 4-ClC$_6$H$_4$ | **30** | 37 | **47.8** | **53.5** | **43.5** |
| 8 | | | | | ABT-751 | | 209.1 | 117.5 | 139.7 |
| 9 | | | | | Indisulam | | 229.1 | 100.6 | 155.8 |

Compound numbers correspond to FIG. 7

Rotenone

2-Deoxyglucose (2DG)

D-Luciferin

Oxyluciferin

SYNTHESIS AND USE OF N-BENZYL SULFONAMIDES

CROSS REFERENCE TO RELATED APPLICATIONS

The present application claims priority to U.S. Provisional Application No. 63/056,211 filed on Jul. 24, 2020, which is incorporated herein by reference.

BACKGROUND

Sulfonamides are a crucial class of bioisosteres that are prevalent in a wide range of pharmaceuticals. Unfortunately, the ability to produce sulfonamides directly from heteroaryl aldehyde reagents remains limited. In particular, methods are needed for the direct installation of sulfonamide functionality on heteroarene scaffolds. This disclosure provides new methods for the production of a wide range of N-benzyl sulfonamides via a one-pot reduction of intermediate N-heteroarene-containing N-sulfonyl imines generated from commercially available aldehydes under mild conditions. Additionally, the following disclosure provides a new approach for regioselective incorporation of a sulfonamide unit to heteroarene scaffolds.

SUMMARY

In one aspect, the present disclosure provides a method of preparing N-benzyl sulfonamides. The method comprises the steps of adding a sulfonamide and a heteroaromatic compound having a functional group such as an aldehyde, alcohol, ketone or amine to a single reaction vessel. The reaction is initiated by adding elemental iodine and an oxidizing agent such as a hypervalent iodine compound to the reaction vessel under non-acidic conditions. The resulting compound is an imine which is then reduced to the desired sulfonamide.

Also provided is a compound for treating cancer comprising a N-benzyl sulfonamide and a metabolic inhibitor.

Also provided is a method for determining the ATP levels of a cell following treatment with a metabolic inhibitor and a N-benzyl sulfonamide.

BRIEF DESCRIPTION OF THE DRAWINGS

FIG. 9 provides the results of the cytotoxicity screening of compounds 2, 5-9, 11-12, 14, 16, 18-22 of FIG. 7 performed according to the prior art method for determining cytotoxicity.

DETAILED DESCRIPTION

Throughout this disclosure, the terms "about", "approximate", and variations thereof, are used to indicate that a value includes the inherent variation or error for the device, system, the method being employed to determine the value, or the variation that exists among the study subjects.

Method for Preparing Sulfonamides from Heteroaryl Aldehydes

Figure 4:
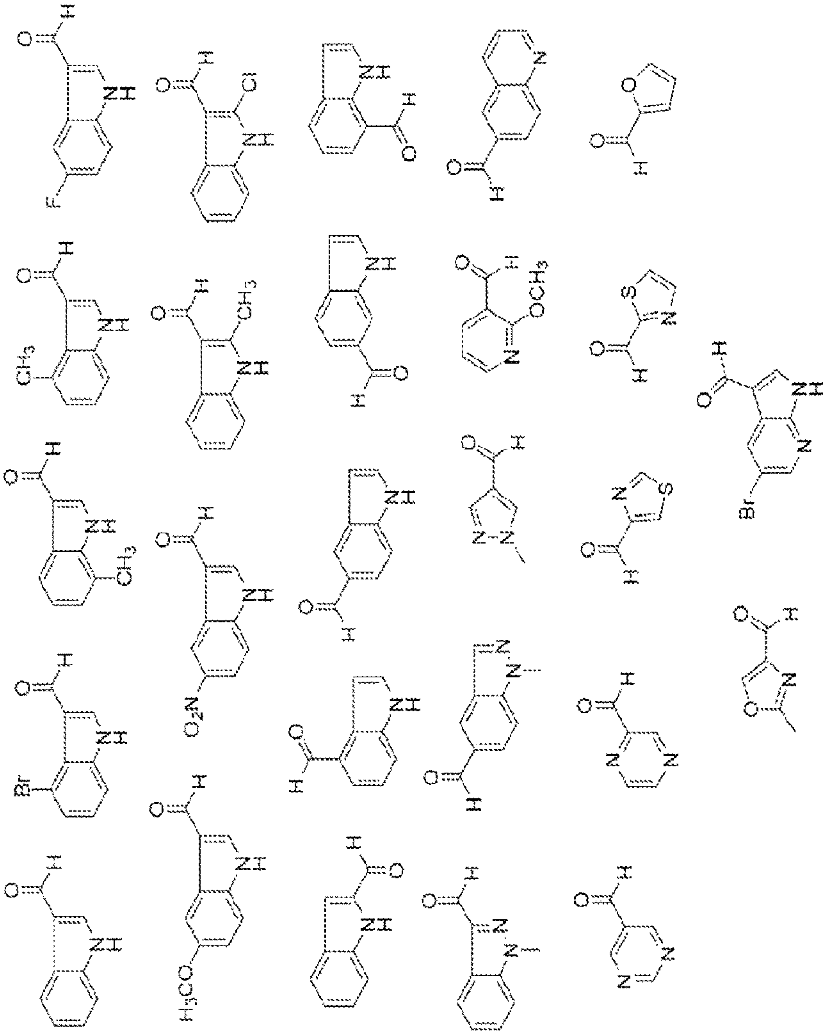
FIG. 4 depicts non-limiting examples of heteroaromatic compounds suitable for use in the present method where $R^2$ of FIG. 1 is an aldehyde or carboxaldehyde.
Figure 5:
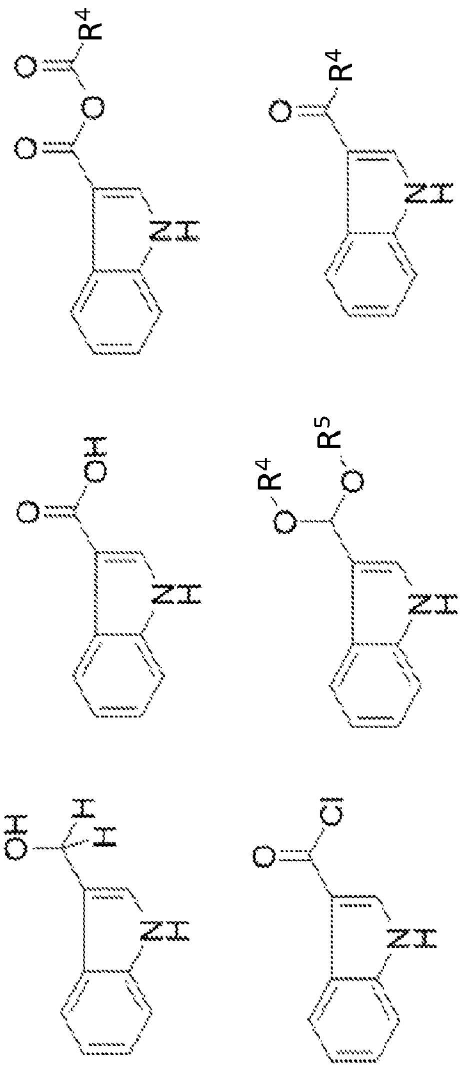
FIG. 5 depicts non-limiting examples of heteroaromatic compounds suitable for use in the present method where $R^2$ of FIG. 1 includes precursors to aldehydes and other carbonyl containing functionalities.
Figure 14:
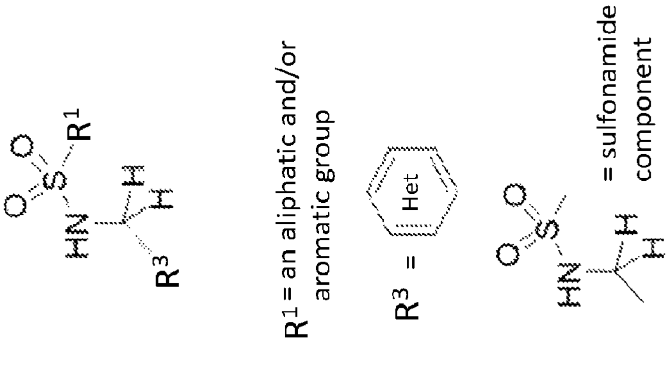
FIG. 14 depicts the structure and components of N-benzyl sulfonamide.
Figure 15:
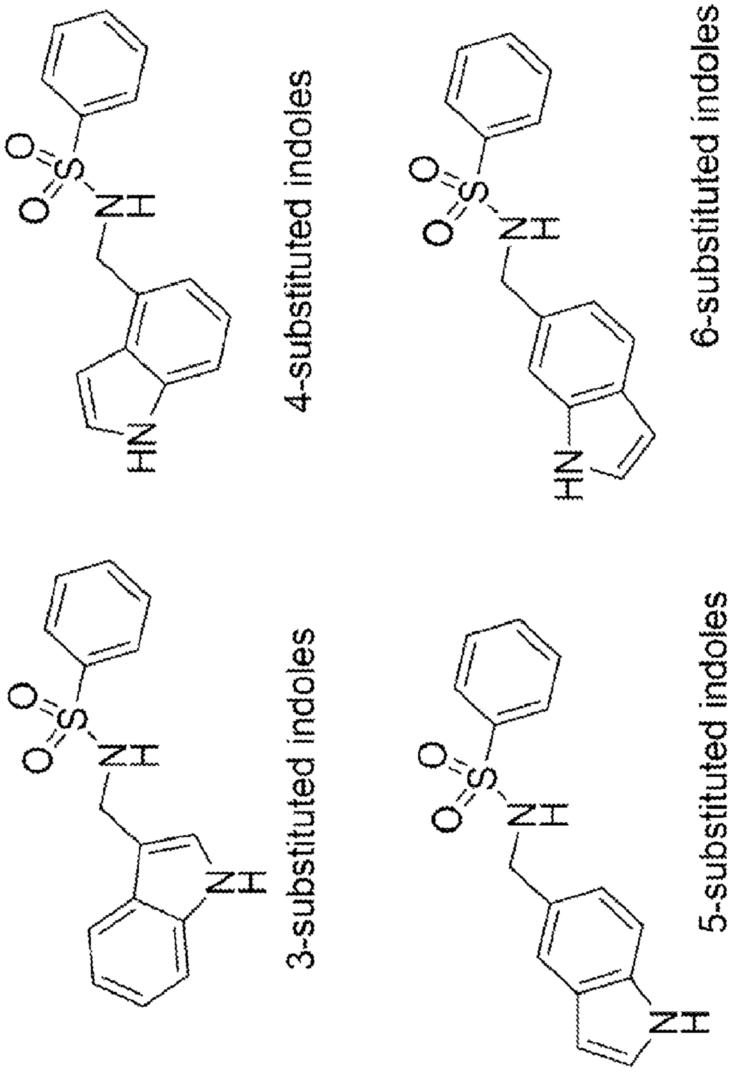
FIG. 15 provides four non-limiting examples of N-benzyl sulfonamides where the $R^3$ group is an indole and the sulfonamide component is attached at different locations on the indole.
Figure 16:
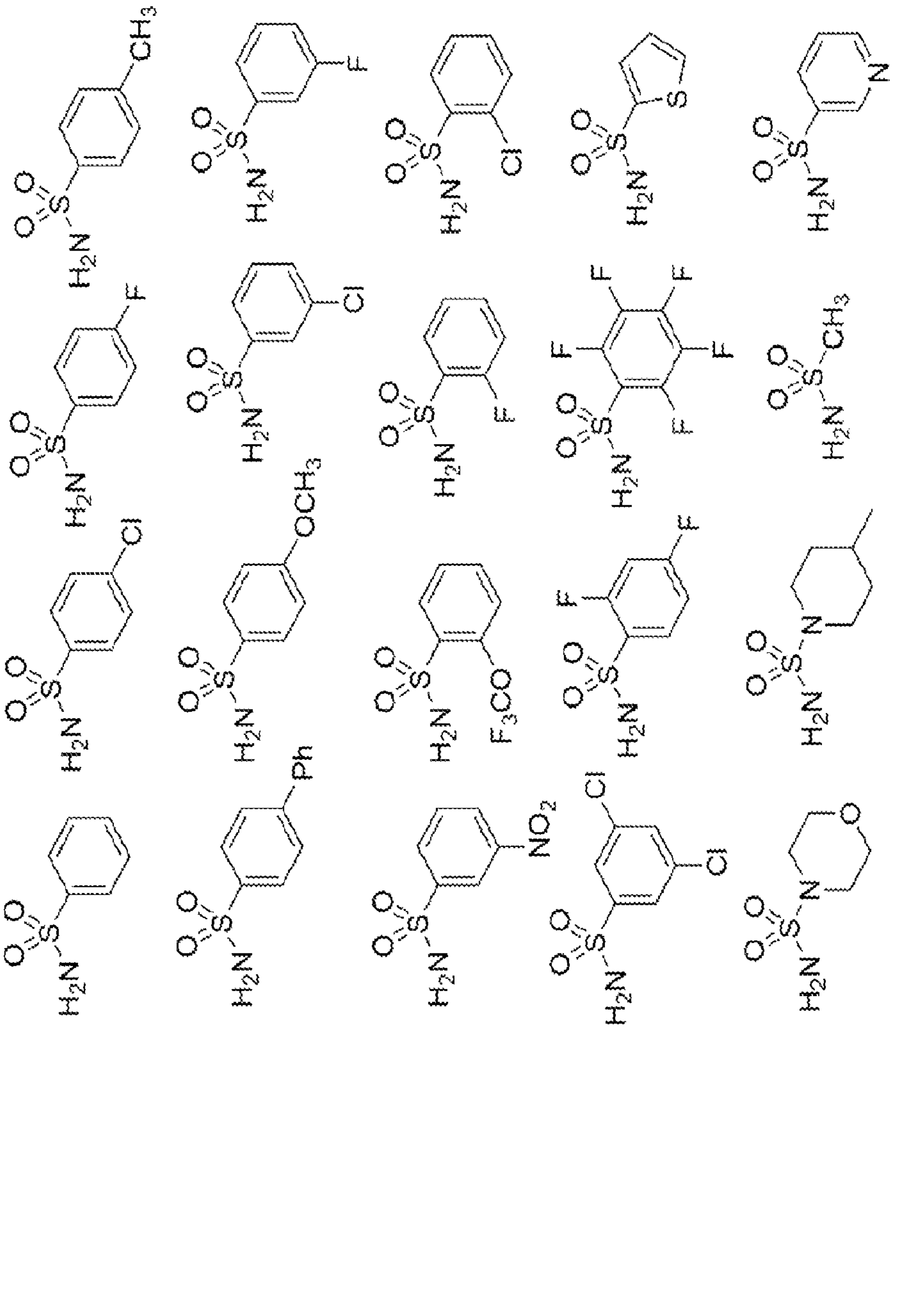
FIG. 16 provides non-limiting examples of the N-substrate.

In one embodiment, the method disclosed reacts a heteroaromatic compound having a functional group such as an aldehyde or precursor to an aldehyde as reflected in FIGS. 4 and 5, with an N-substrate, i.e. nitrogen containing substrate, in the form of a sulfonamide in the presence of elemental iodine ($I_2$) and an oxidizing agent such as a hypervalent iodine compound to form N-sulfonyl imines, under non-acidic conditions, on the heteroaromatic scaffold of the heteroaromatic compound. The N-substrate includes functional group $R^1$ which may be an aromatic, heteroaromatic or aliphatic group. The functional group $R^1$ will be of the final N-benzyl sulfonamide. The combination of iodine and an iminoiodinane reagent direct the replacement of the original $R^2$ functional group on the heteroaromatic compound with the intermediate deactivated imine from the sulfonamide on the heteroaromatic scaffold. Subsequently, the intermediate deactivated imine is converted by a reducing agent to a sulfonamide. This approach provides for addition of sulfonamides on heteroaromatic scaffolds having basic sites. As known to those skilled in the art, heteroaromatic scaffolds having basic sites preclude traditional acid-dependent reactive pathways from occurring. FIG. 14 depicts the primary components of the resulting N-benzyl sulfonamide and FIG. 15 provides generic structural examples of different locations suitable for attachment of the benzylic sulfonamide to the heteroarene, i.e. the attachment point on the $R^3$ heteroaromatic group.

Figure 2:
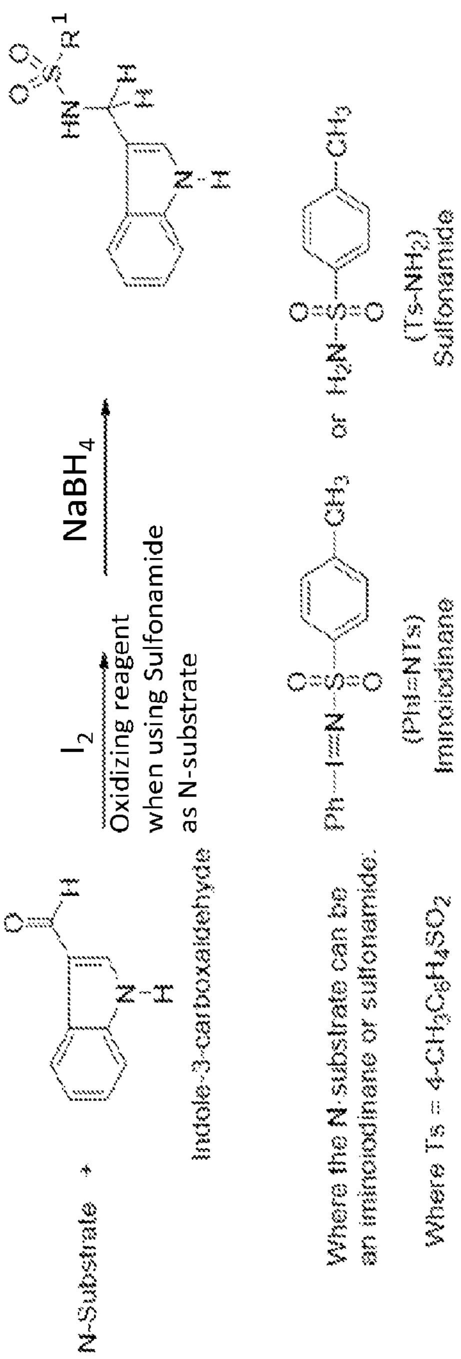
FIG. 2 provides an example of the formation of a sulfonamide on the indole-3-carboxaldehyde scaffold.

Alternatively, the step of converting the sulfonamide to an iminoiodinane in situ can be skipped. In this case the iminoiodinane reagent can be prepared in advance of the reaction and used as the N-substrate as reflected in FIG. 2, provided that the iminoiodinane compound contains a nitrogen molecule at the proper location. Examples of such compounds are provided in FIG. 3. When using iminoiodinane reagent as the N-substrate a separate oxidizing agent is not required. However, in general, the preferred method will be to use a sulfonamide as the N-substrate and to convert the sulfonamide to the imine prior to using the reducing agent.

A non-limiting list of suitable hypervalent iodine reagents for use in the present method would include: phenyliodine (III) diacetate ($PhI(OAc)_2$), phenyliodine bis(trifloroacetate) (PIFA), iodosylbenzene (PhIO), [hydroxyl(tosyloxy)iodo] benzene (HTIB, Koser reagent), $PhICl_2$, $TolIF_2$, diaryl iodonium salts, Togni's reagents, μ-oxobis(trifluoroacetoxyiodobenzene) (μ-oxo BTI), Dess-Martin periodinane, 2-Iodoxybenzoic acid (IBX), cyano(trifluoromethylsulfonyloxy)iodobenzene (Stang's reagent), 1-phenyl-2-(phenyl-$\lambda^3$-iodaneylidene)-2-((trifluoromethyl)sulfon-yl)ethan-1-one (Shibata reagent II), iodosodilactone. In general, any hypervalent iodine compound will function in the reactions described herein provided that it serves as an oxidizing agent to form intermediate iminoiodinane in conjunction with a sulfonamide reagent.

A non-limiting list of heteroaromatic compounds suitable for use in the following method include but are not limited to those structures identified in FIGS. 4 and 5. In general, the heteroaromatic compounds suitable for conversion to sulfonamides will have an aldehyde functionality or a carboxaldehyde functionality. A particularly desired heteroaromatic compound for use in this method is an indole. Other heteroaromatic compounds suitable for forming sulfonamides include, but are not limited to: carboxaldehydes with indazole and pyrazole cores; aldehyde substrates that contain 6-membered N-heteroarenes such as pyridine, quinoline, pyrimidine, pyrazine; benzylic amines; benzylic alcohols; and, thiazole, oxazole, and furan scaffolds. Additionally, the method disclosed herein may be carried out with functionalities such as aryl halide, amide, sulfonamide, aryl ether, benzylic C—H bonds, and C—H bonds adjacent to carbonyls and heteroatoms in place of the aldehyde and carboxaldehyde functionality.

Reducing agents appropriate for use in the following method include but are not limited to: sodium borohydride, lithium aluminum hydride, lithium borohydride, diisobutyl aluminum hydride, sodium cyanoborohydride, sodium triacetoxyborohydride, 9-borabicyclo(3.3.1)nonane (9-BBN), and Hantzsch ester. Those skilled in the art will be familiar with other approaches for reducing the sulfonyl imine to the sulfonamide. For example, a catalytic reduction in the presence of hydrogen will perform satisfactorily.

Figure 1:
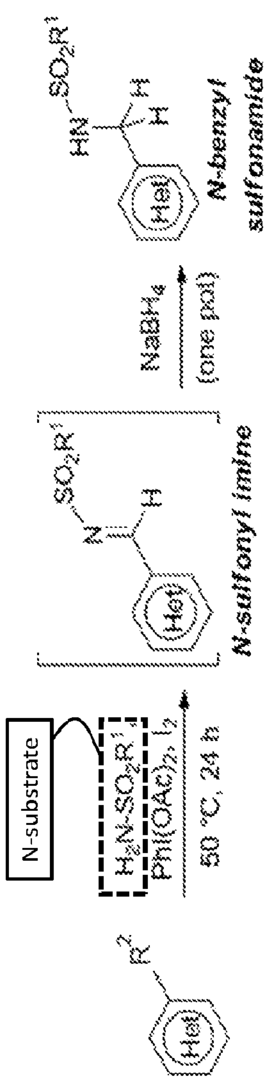
FIG. 1 depicts the two-step formation of primary N-benzyl sulfonamides.
Figure 3:
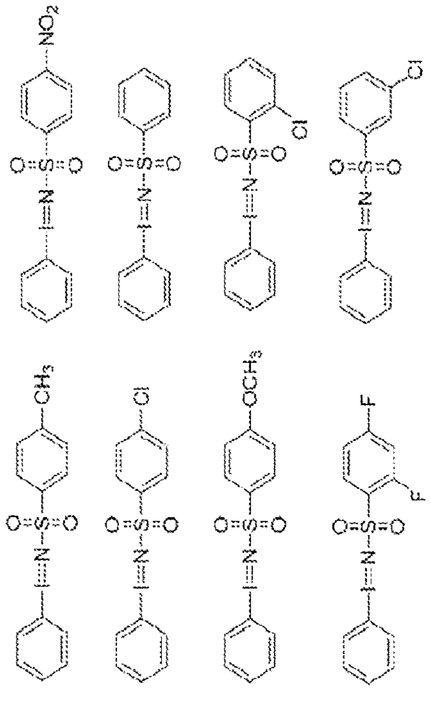
FIG. 3 depicts non-limiting examples of iminoiodinane reagents suitable for use in the present method.

FIGS. 1 and 2 provide examples of the method for converting $R^3$ a heteroaromatic compound having a functionality —$R^2$— to a sulfonamide. In FIG. 2, the $R^2$ functionality is the aldehyde portion of indole-3-carboxaldehyde; however, $R^2$ may also be a ketone or a precursor to an aldehyde or a ketone. When using a heteroaromatic compound with $R^2$ as a precursor to an aldehyde or a ketone, the initial step will be conversion of the precursor to an aldehyde or ketone such that the sulfonamide will react at the desired location on the heteroaromatic compound. When the reaction is carried out in accordance with the method described below, the aldehyde or ketone functionality is converted to an imine and then reduced to the sulfonamide functionality. In most instances, the N-substrate will be a sulfonamide that is converted to an imine followed by reduction to the desired compound. However, as noted above, an iminoiodinane compound as depicted in FIG. 3 may be used in which case the oxidizing agent will not be required. The remaining discussion focuses on the two-step method using a sulfonamide as the N-substrate. The wide variety of sulfonamides suitable for use in the present method can be seen as the functional groups in FIG. 7 that have replaced the aldehyde or ketone functionality on the heteroaromatic compound.

As discussed above, the two-step method utilizes $R^3$, a heteroaromatic compound having a functional group $R^2$ capable of reacting with the N-sulfonamide component of the N-substrate. FIGS. 4 and 5 provide non-limiting examples of suitable heteroaromatic compounds. When the heteroaromatic compound ($R^3$) has an aldehyde or ketone functionality as $R^2$, the first step of the reaction involves combining the selected heteroaromatic compound with the selected N-substrate along with a hypervalent iodine reagent and elemental iodine in a solvent. In FIG. 5, $R^4$ and $R^5$ may be an alkyl group or an aryl group, such as, but not limited to: methyl, ethyl, propyl, isopropyl, butyl, isobutyl, tert-butyl, phenyl, benzyl. Suitable solvents include, but are not limited to: chloroform, dichloromethane, or dichloroethane. The amount of solvent used is sufficient to dissolve or suspend all reactants. A typical combination will involve the following ratios of components: two to five equivalents of the heteroaromatic compound; one equivalent of the N-substrate (i.e., a sulfonamide); two equivalents of a hypervalent oxidizing reagent; and, one equivalent of elemental iodine.

The reaction takes place over a period of about 8 to about 48 hours with stirring or mixing at a temperature of about 20° C. to about 60° C. under an atmosphere that is inert to the reactants. Typically, the reaction takes place over a period of about 18 hours to 26 hours with stirring or mixing at a temperature of about 40° C. to about 60° C. under argon gas. Other gases suitable for use in this method would include: nitrogen or air. Following the reaction period, the reaction products are typically cooled to room temperature, e.g. a temperature of about 17° C. to about 22° C., followed by removal of the any remaining liquid component. The remaining solid material is dissolved in a mixture of methanol and dichloromethane and cooled to a room temperature, e.g. about 17° C. to about 22° C. Alternative solvents for use in this step include, but are not limited to: ethanol, isopropyl alcohol, chloroform, ethyl acetate, diethyl ether, acetonitrile, tetrahydrofuran, and dichloroethane. The amount of solvent used in this step is not critical. In general, that amount sufficient to completely dissolve the reaction products will be used. The first step of the reaction process is complete when the intermediate imine product is formed. The presence of the sulfonyl imine product can be confirmed by nuclear magnetic resonance (1H NMR, 13C NMR) and mass spectrometry.

Following dissolution of the initial reaction products in solvent, the conversion of the sulfonyl imine intermediate to the sulfonamide occurs by a reduction reaction. In most instances, the reduction of the sulfonyl imine intermediate can take place in the same reaction vessel as the first step. Thus, the preparation of the sulfonamide on heteroaromatic scaffold can be referred to as a "one pot" method. The reduction of imine to sulfonamide is brought about by stepwise addition of a reducing agent, such as sodium borohydride, to the reaction vessel while the reaction vessel is at a temperature less than 40° C. Approximately, 5 equivalents of sodium borohydride are added over a period of 1-5 minutes followed by 10 minutes of stirring. Then a second portion of 5 equivalents of sodium borohydride is added over a period of 1-5 minutes followed by an additional 10 minutes of stirring. The desired temperature during the addition of the reducing agent is that temperature which prevents potential decomposition of the product. After approximately 10 minutes to about 45 minutes the solution is allowed to warm to room temperature or a temperature of about 20° C. with continued stirring or mixing. Any remaining reducing agent is neutralized by addition of water. A solvent extraction process is used to isolate the resulting sulfonamide which is subsequently dried by treatment with sodium sulfate under a vacuum. Final purification of the sulfonamide can be performed by flash chromatography or any other convenient method such as recrystallization. Typical flash chromatography will use a blend of hexanes and ethyl acetate as the eluent. Advantageously, the reaction pathways of the present method preclude the formation of byproducts such as would occur under benzylic amidation via C—H activation.

Figure 6:
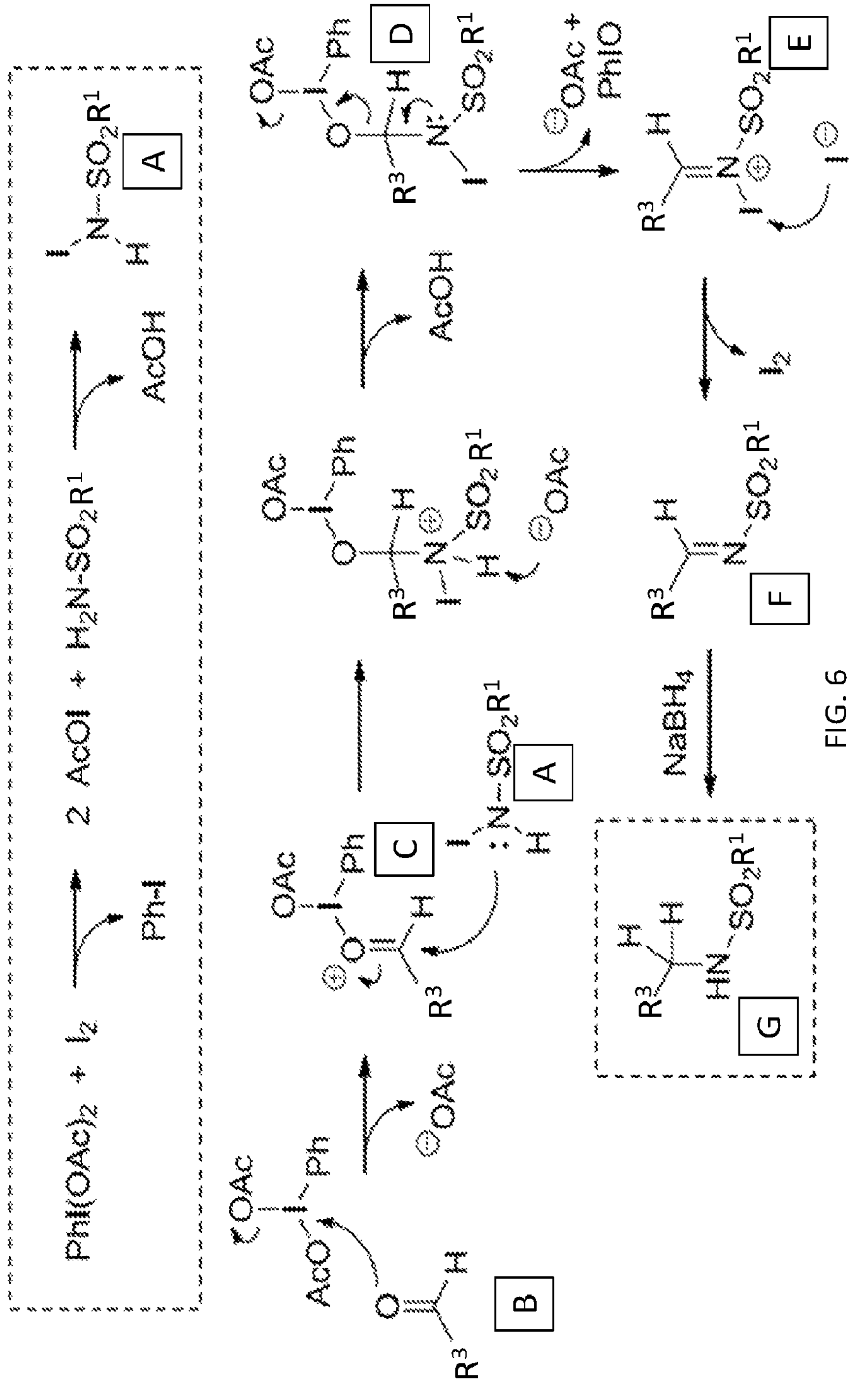
FIG. 6 depicts the theorized mechanism of attaching the sulfonamide function to the heteroaromatic compound.
Figure 7A:
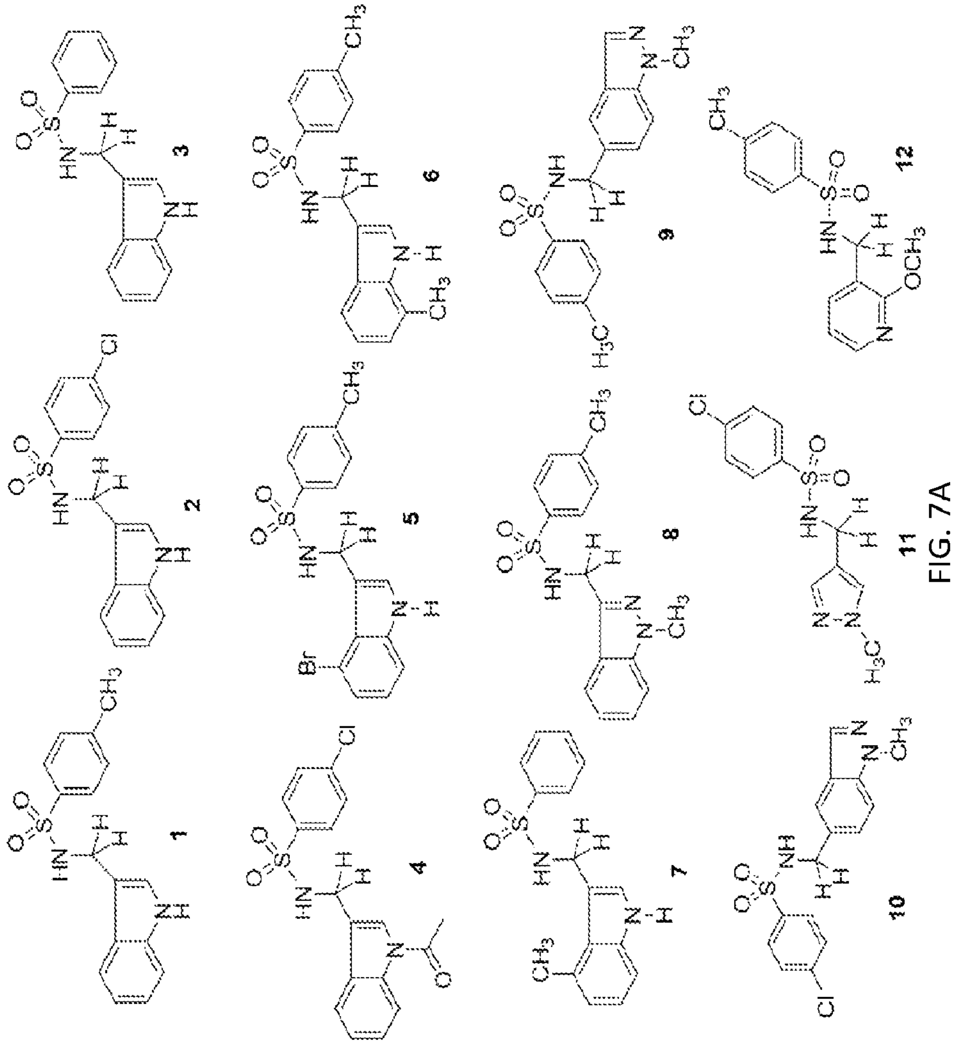
FIGS. 7A-7L provide the chemical structures of the N-benzyl sulfonamides identified in FIG. 10 as well as other N-benzyl sulfonamides.
Figure 7B:
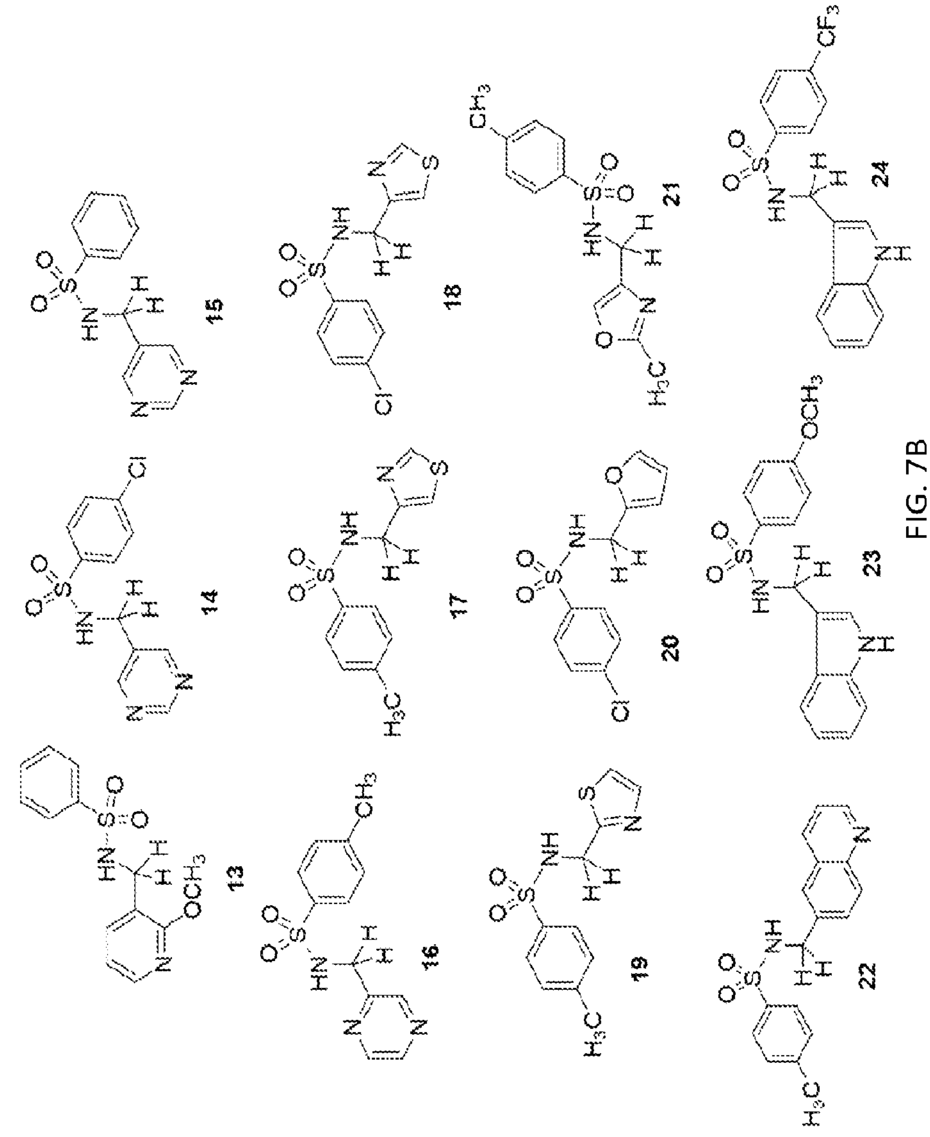
Figure 7C:
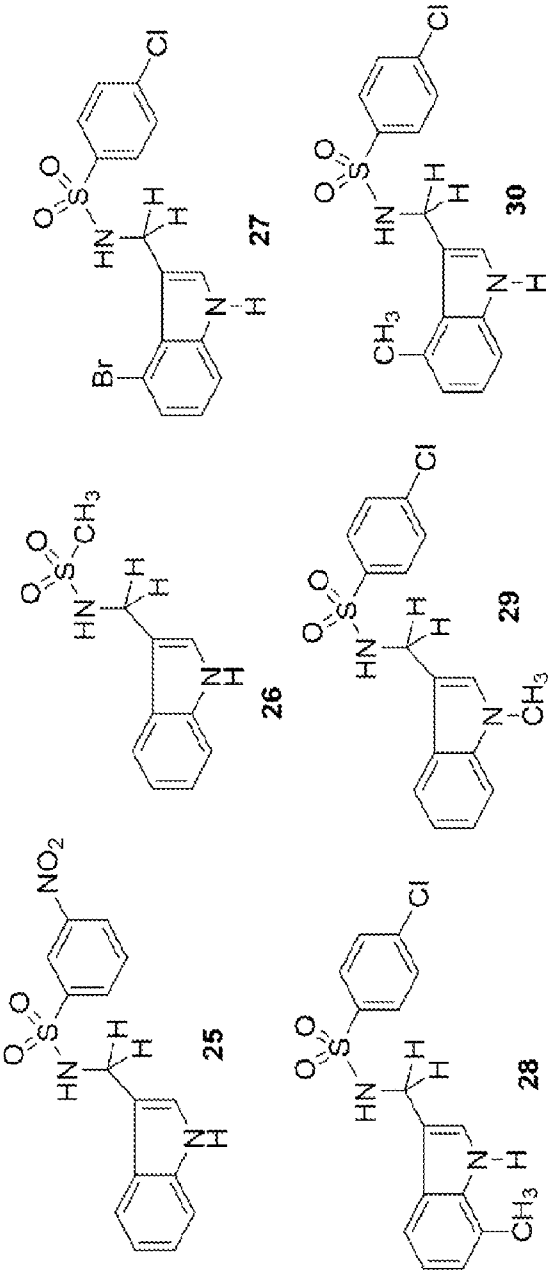
Figure 7D:
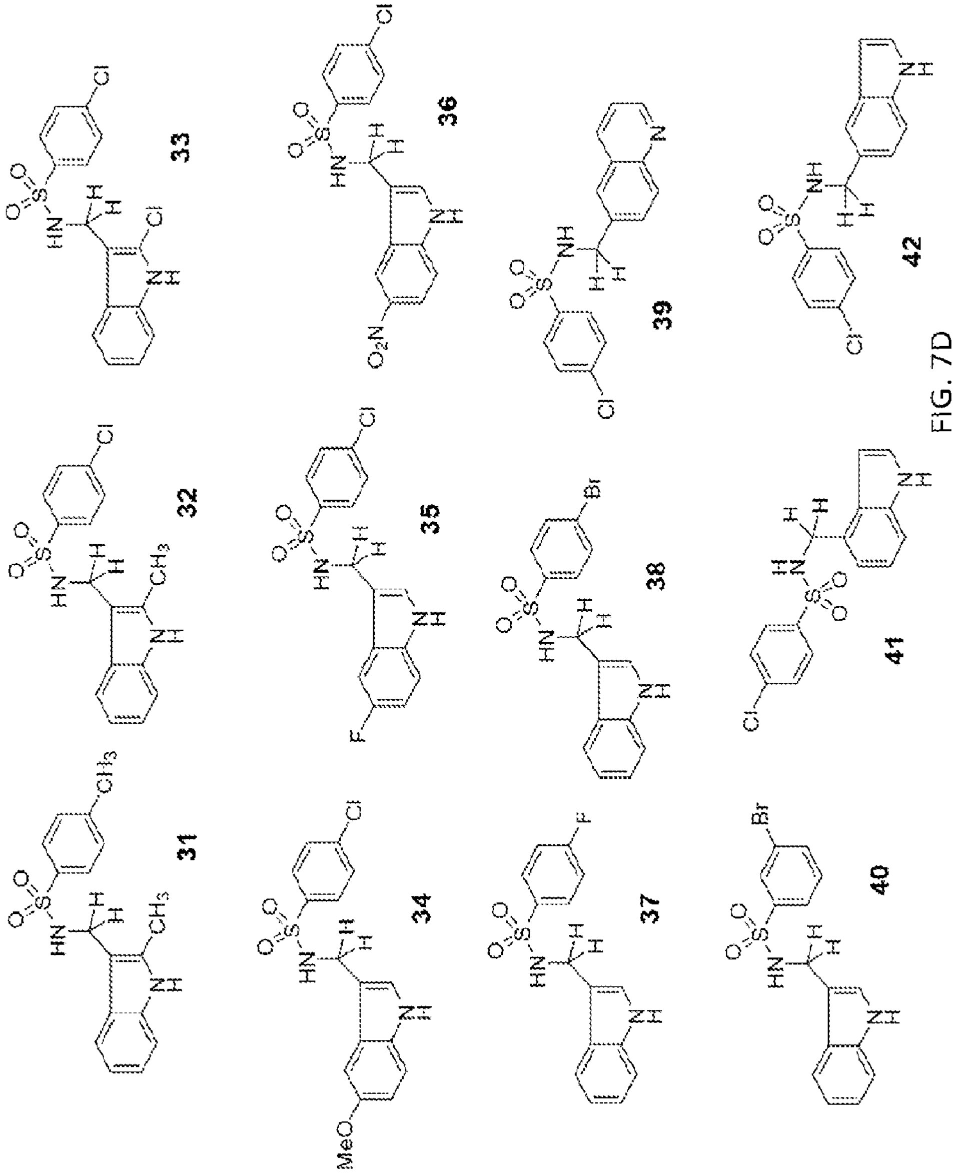
Figure 7E:
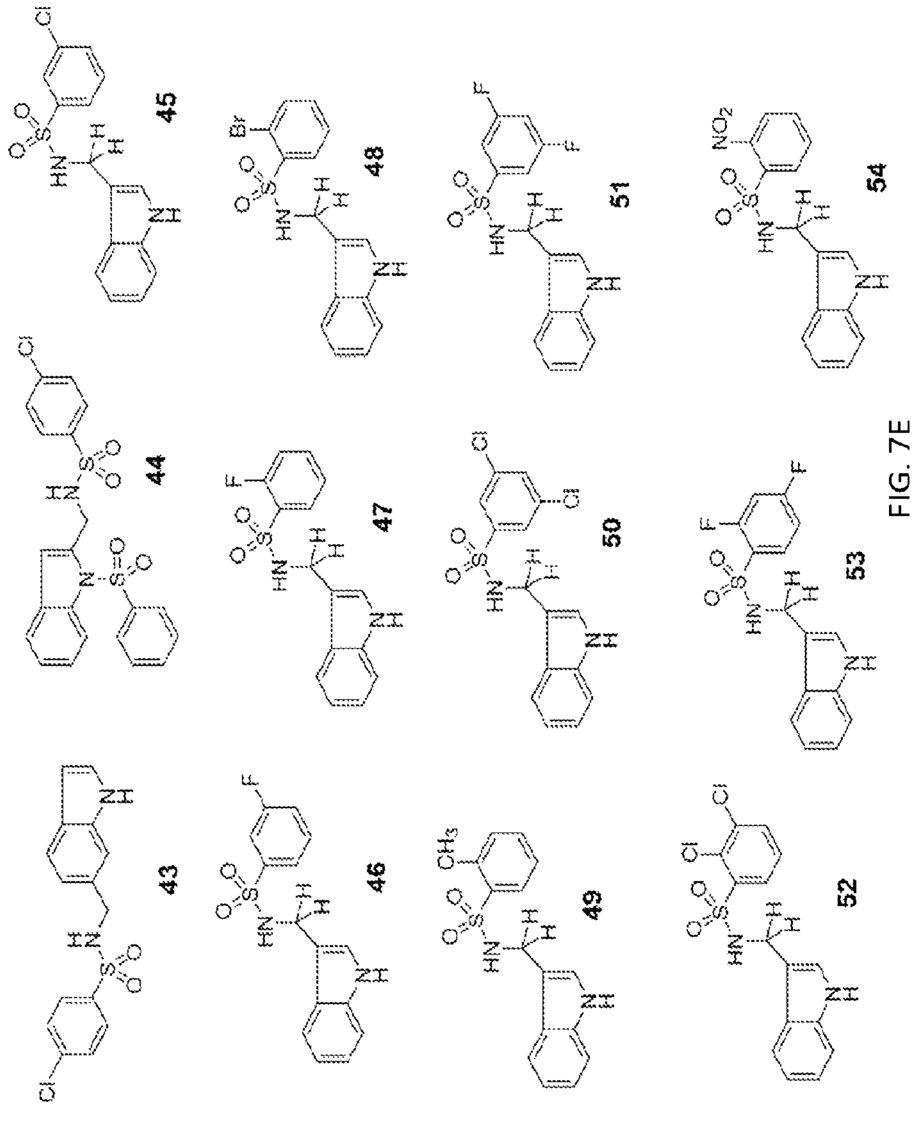
Figure 7F:
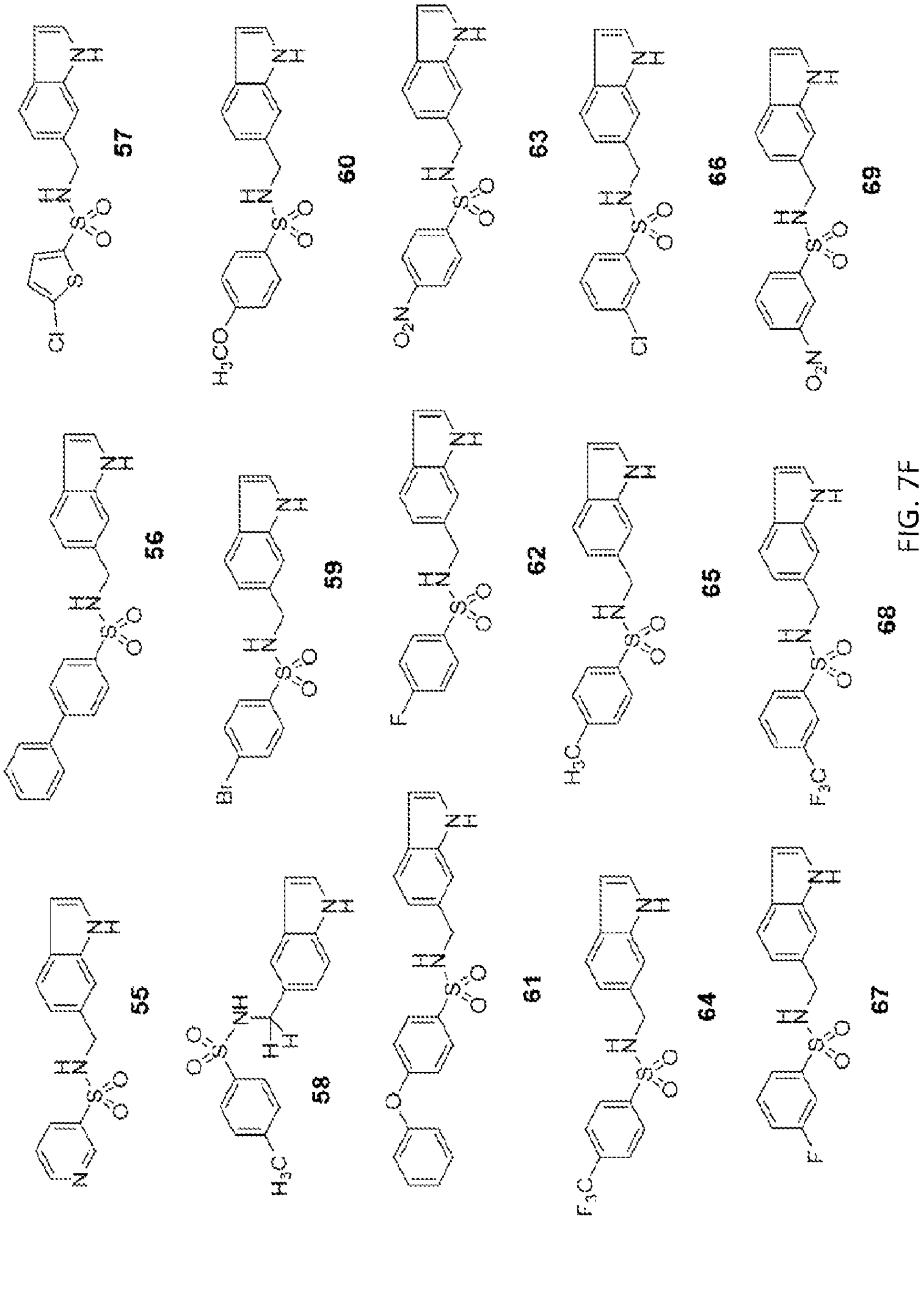
Figure 7G:
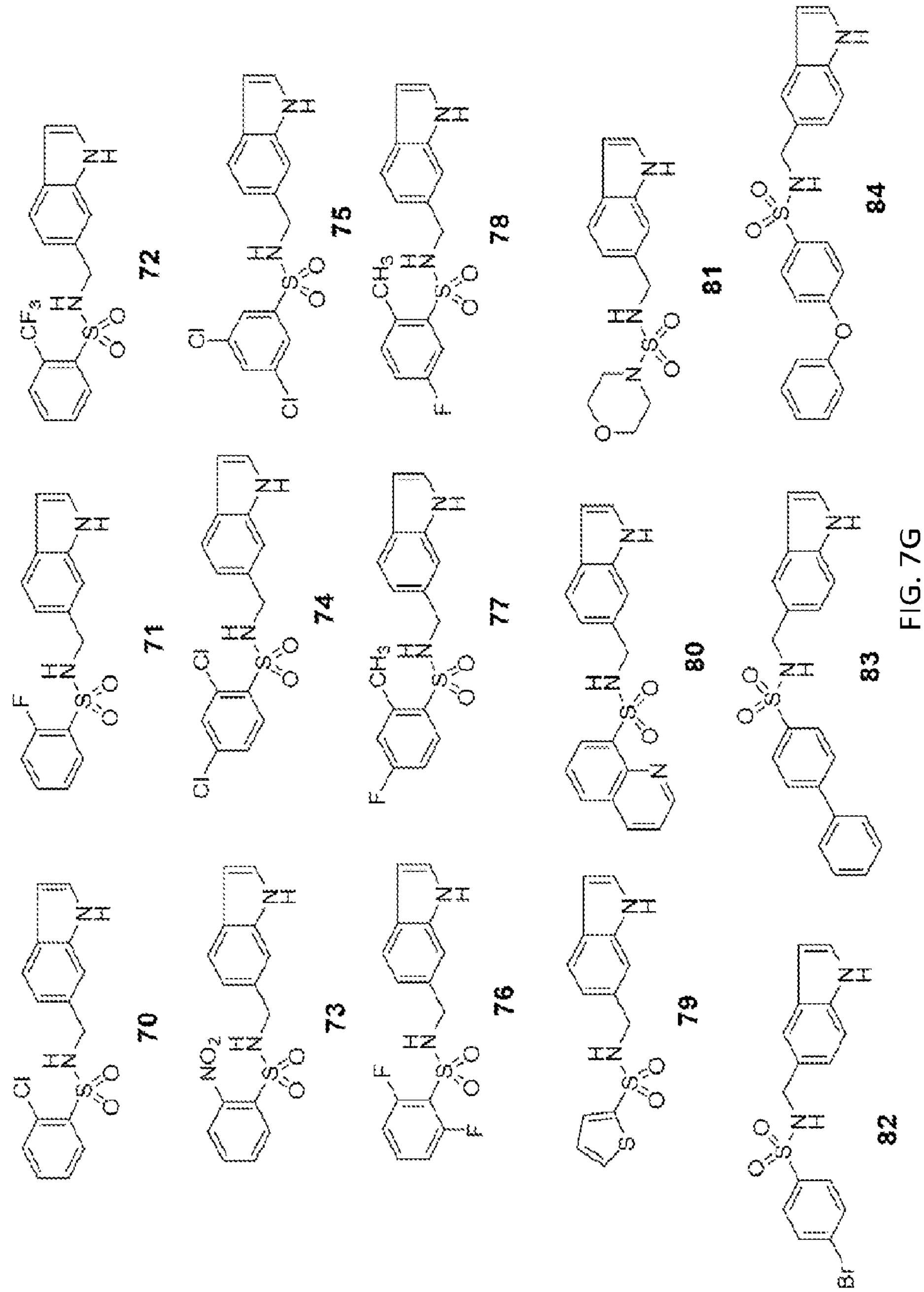
Figure 7H:
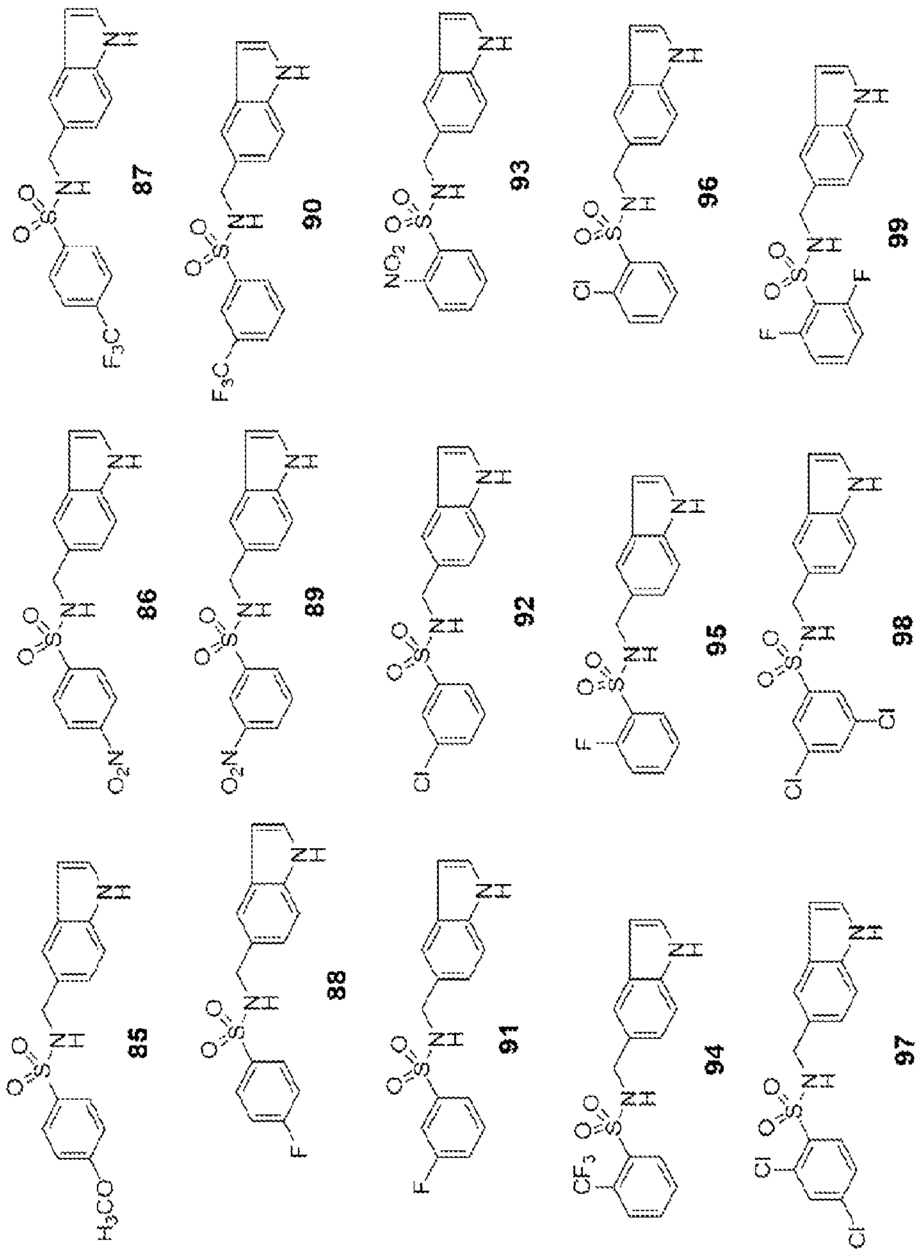
Figure 7I:
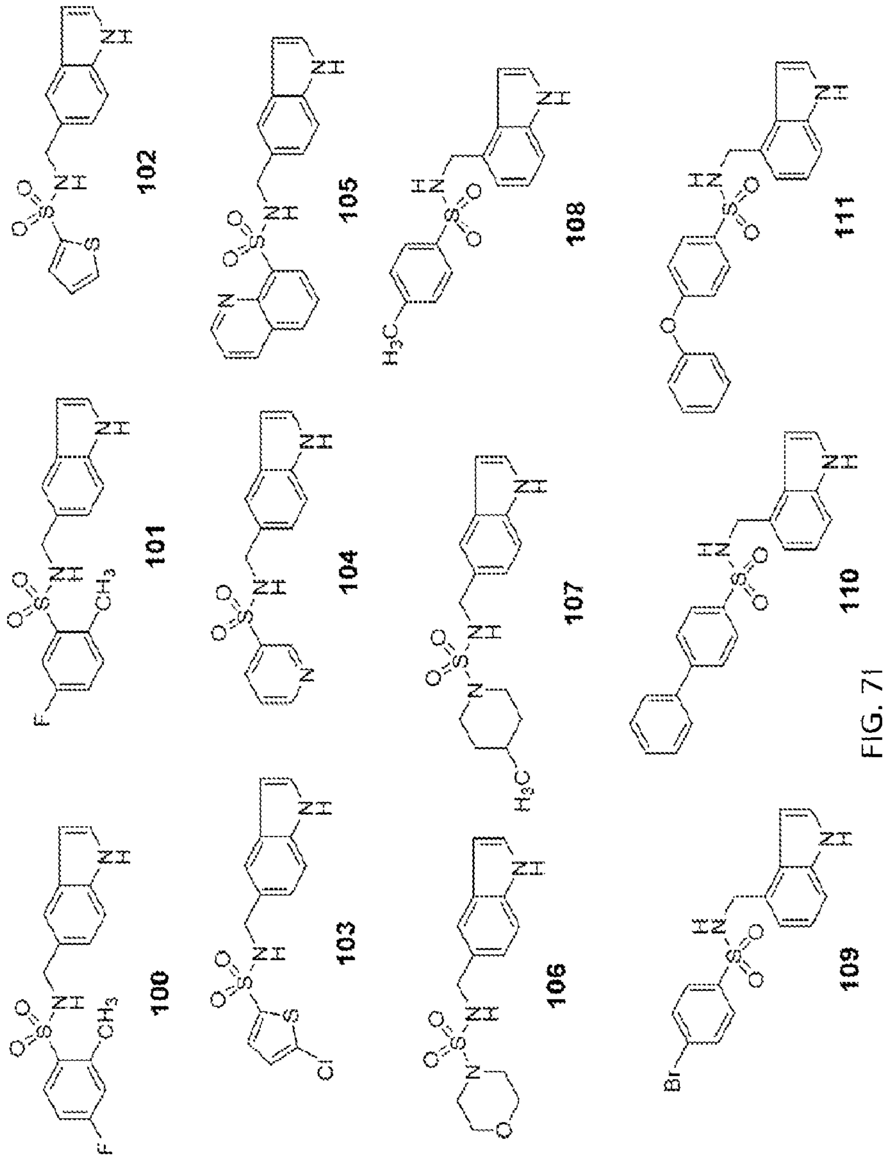
Figure 7J:
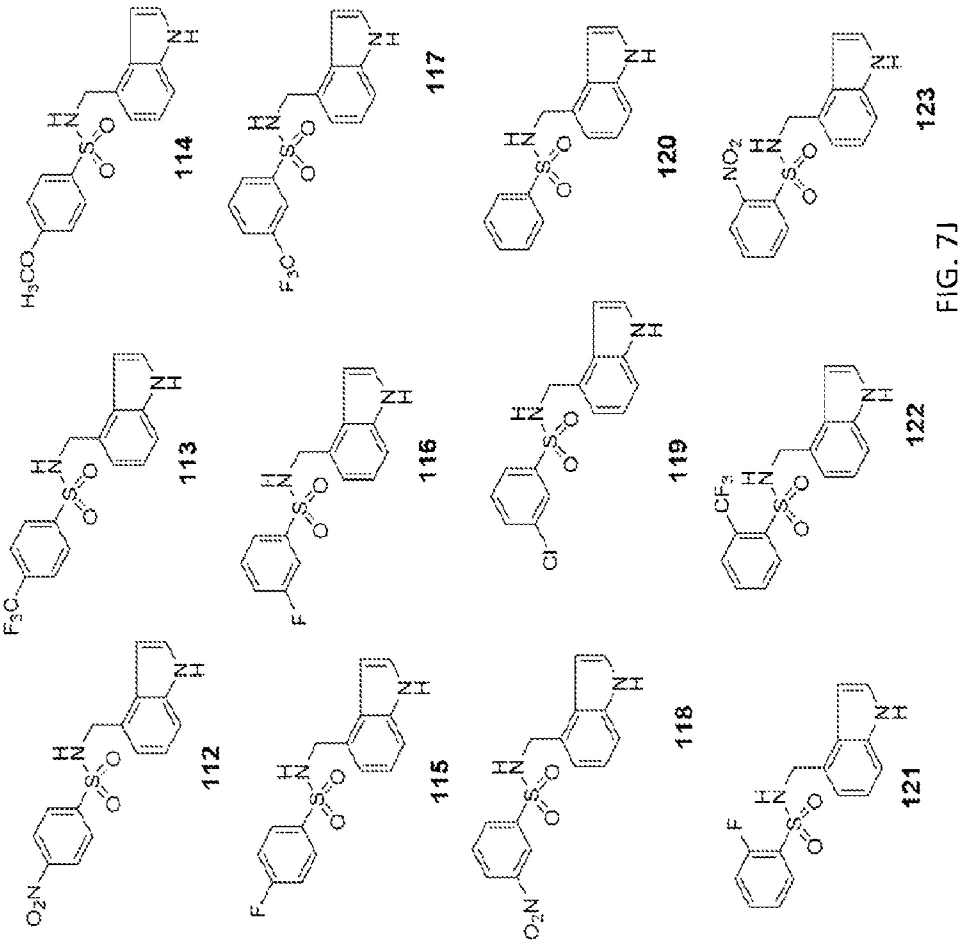
Figure 7K:
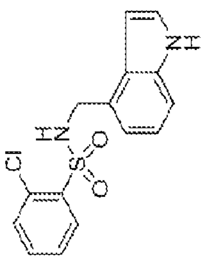
Figure 7K:
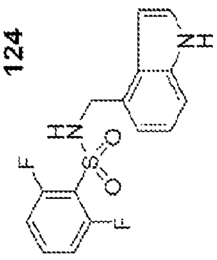
Figure 7K:
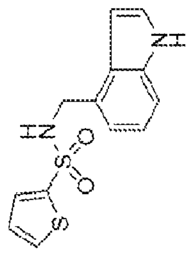
Figure 7K:
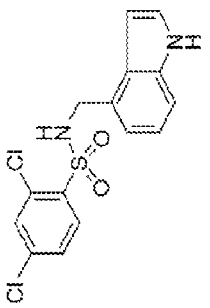
Figure 7K:
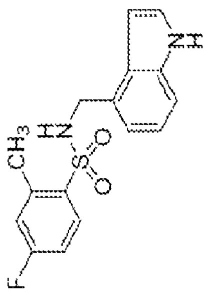
Figure 7K:
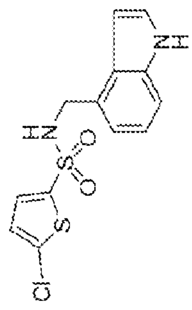
Figure 7K:
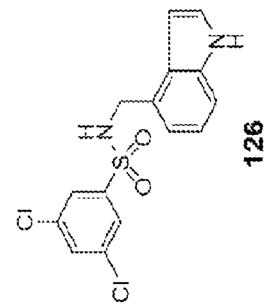
Figure 7K:
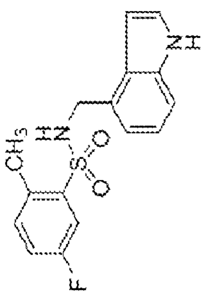
Figure 7K:
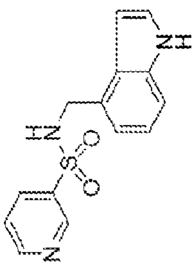
Figure 7L:
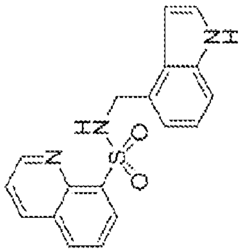
Figure 7L:
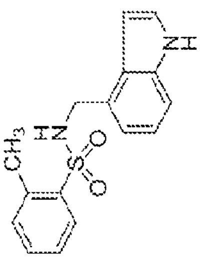
Figure 7L:
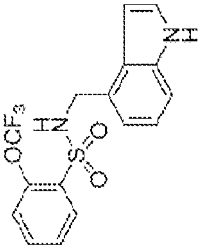
Figure 7L:
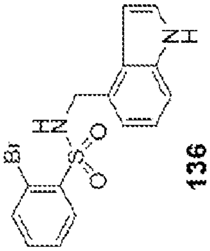
Figure 7L:
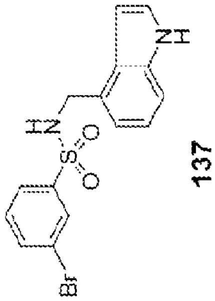
Figure 7L:
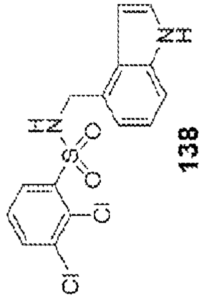
Figure 7L:
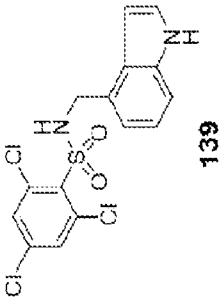

Without intending to be bound by theory and simply to provide a better understanding of the reactions described herein, FIG. 6 depicts a plausible mechanism for the attachment of the sulfonamide functionality to the heteroaromatic scaffold. As outlined in FIG. 6, the formation of N-benzyl sulfonamide from phenyliodine(III) diacetate ($PhI(OAc)_2$), elemental iodine, and sulfonamide is believed to proceed according to the following steps: 1) an enhanced product yield results when using an excess of aldehyde substrate (e.g. 2 to 5 equivalents), with 2) either a stoichiometric or catalytic amount of iodine. The formation of Acetyl hypoiodite (AcOI), a source of electrophilic "I+", is known to occur from the combination of $PhI(OAc)_2$ and elemental iodine. In the presence of sulfonamide, AcOI generates an N-iodosulfonamide (A). The addition of iodine serves to reduce the nucleophilic strength of the sulfonamide nitrogen. Masking of the sulfonamide, along with the use of an excess of aldehyde substrate, allows the aldehydic oxygen atom (B) of the heteroaromatic group $R^3$ to coordinate the electrophilic center of $PhI(OAc)_2$. The sulfonamide (A) with functional group $R^1$ then attacks the electron-deficient carbonyl carbon (C) leading to intermediate (D). Loss of iodosylbenzene (PhIO) and acetate to produce intermediate (E) would occur with complete retention of the aldehydic C—H bond. Molecular iodine is regenerated in the formation of imine (F), which accounts for the ability to perform the reaction using a catalytic amount of elemental iodine. The resulting N-sulfonyl imine (F) is then reduced with $NaBH_4$ to form N-benzyl sulfonamide product (G) where $R^3$ represents the heteroaromatic group as discussed above.

Preparation of Example Compounds 1-139 as Depicted in FIG. 7

The following examples demonstrate the use of a variety of heteroaromatic compounds as the $R^3$ scaffold material for production of N-benzyl-sulfonamides and a variety of N-substrates with functional groups $R^1$. The final products are depicted as compounds 1-30 in FIG. 7. The compounds were prepared using the method outlined above and the materials identified. The number in parentheses appearing after the title of the compound identifies the corresponding structure in FIG. 7.

N-[(1H-indol-3-yl)methyl]-4-methylbenzenesulfonamide (1). The title compound was prepared according to the general procedure. Brown-red solid (24 mg, 61%): m.p. 140-144° C.; purification (hexanes:EtOAc, 60:40), $R_f$=0.42. $^1$H NMR (400 MHz, $CDCl_3$): δ=8.06 (bs, 1H), 7.79 (dt, J=8.2 Hz, J=2.0 (×2) Hz, 2H), 7.40 (dd, J=8.0, 1.0 Hz, 1H), 7.35-7.29 (m, 3H), 7.20 (ddd, J=8.2, J=7.0, J=1.2 Hz, 1H), 7.08 (ddd, J=8.2, J=7.0, J=1.2 Hz, 1H), 7.05 (d, J=2.3 Hz, 1H), 4.47 (bt, J=5.5 Hz, 1H), 4.32 (d, J=5.5 Hz, 2H), 2.45 (s, 3H) ppm. $^{13}$C NMR (100 MHz, $CDCl_3$): δ=143.4, 136.7, 136.2, 129.7, 127.3, 126.1, 123.3, 122.7, 120.0, 118.6, 111.3, 111.0, 39.0, 21.6 ppm. IR (neat): v=3377, 3275, 3059, 2921, 1724, 1596, 1287, 1153, 1021, 744 cm$^1$. HRMS (ESI): calculated for $C_{16}H_{17}N_2O_2S_1$ $[M+H]^+$ requires m/z 301.10108, found m z 301.06378.

N-[(1H-indol-3-yl)methyl]-4-chlorobenzenesulfonamide (2). The title compound was prepared according to the general procedure from 1H-indole-3-carbaldehyde (1.25 mmol, 5 equiv), 4-chlorobenzenesulfonamide (0.25 mmol, 1 equiv.), iodobenzene diacetate (0.5 mmol, 2 equiv.), 12 (0.25 mmol, 1 equiv.) in $CHCl_3$ (3 mL). Brown-red solid (48 mg, 60%): m.p. 154-158° C.; purification (hexanes:EtOAc, 70:30), $R_f$=0.22. $^1$H NMR (400 MHz, $CDCl_3$): δ=8.05 (bs, 1H), 7.79 (dt, J=8.6 Hz, J=2.0 (×2) Hz, 2H), 7.47-7.39 (m, 3H), 7.34 (d, J=8.2 Hz, 1H), 7.21 (ddd, J=8.2, J=7.4, J=1.2 Hz, 1H), 7.10 (ddd, J=7.8, J=7.0, J=0.8 Hz, 1H), 7.05 (d, J=2.3 Hz, 1H), 4.56 (bt, J=5.5 Hz, 1H), 4.36 (d, J=5.5 Hz, 2H) ppm. $^{13}$C NMR (100 MHz, $CDCl_3$): δ=139.0, 138.4, 136.2, 129.2, 128.6, 126.0, 123.4, 122.8, 120.2, 118.5, 111.4, 110.7, 39.1 ppm. IR (neat): v=3406, 3281, 3093, 2918, 2849, 1699, 1418, 1317, 1157, 1014, 824, 742 cm$^{-1}$. HRMS (ESI): calculated for $C_{15}H_{14}N_2O_2S_1Cl_1$ $[M+H]^+$ requires m z 321.04645, found m/z 321.04547.

N-[(1H-indol-3-yl)methyl]benzenesulfonamide (3). The title compound was prepared according to the general procedure. Tan solid (22 mg, 60%): m.p. 132-140° C.; purification (hexanes:EtOAc, 60:40), $R_f$=0.33. $^1$H NMR (400 MHz, $CDCl_3$): δ=8.05 (bs, 1H), 7.93-7.89 (m, 2H), 7.62-7.57 (m, 1H), 7.55-7.49 (m, 2H), 7.39 (d, J=8.2 Hz, 1H), 7.34 (d, J=8.2 Hz, 1H), 7.20 (ddd, J=8.2 Hz, J=7.4 Hz, J=1.2 Hz, 1H), 7.08 (ddd, J=8.2 Hz, J=7.0 Hz, J=1.2 Hz, 1H), 7.03 (d, J=2.3 Hz, 1H), 4.51 (bt, J=5.1 Hz, 1H), 4.35 (d, J=5.1 Hz, 2H) ppm. $^{13}$C NMR (100 MHz, $CDCl_3$): δ=139.8, 136.2, 132.6, 129.1, 127.2, 126.1, 123.3, 122.7, 120.1 118.6, 111.3, 110.9, 39.0 ppm. IR (neat): v=3394, 3242, 2918, 1700, 1447, 1423, 1333, 1224, 1153, 730 cm$^{-1}$. HRMS (ESI): calculated for $C_{15}H_{15}N_2O_2S_1$ $[M+H]^+$ requires m/z 287.08543, found m/z 287.08429.

N-[(1-acetyl-1H-indole-3-yl)methyl]-4-chlorobenzenesulfonamide (4). The title compound was prepared according to the general procedure. Off-white solid (30 mg, 64%): m.p. 176-180° C.; purification (hexanes:EtOAc, 60:40), $R_f$=0.29. $^1$H NMR (400 MHz, $CDCl_3$): δ=8.36 (bd, J=8.2 Hz, 1H), 7.78 (dt, J=8.6 Hz, J=2.0 (×2) Hz, 2H), 7.44 (dt, J=8.6 Hz, J=2.0 (×2) Hz, 2H), 7.41 (d, J=7.4 Hz, 1H), 7.36 (ddd, J=8.3 Hz, J=7.1 Hz, J=1.4 Hz, 1H), 7.28-7.23 (m, 2H), 4.80 (bt, J=5.5 Hz, 1H), 4.31 (d, J=5.5 Hz, 2H), 2.55 (s, 3H) ppm. $^{13}$C NMR (100 MHz, $CDCl_3$): δ=168.3, 139.4, 138.2, 135.9, 129.4, 128.6, 128.5, 125.9, 123.9, 118.7, 117.2, 116.8, 38.8, 23.9 ppm. IR (neat): v=3222, 3112, 2924, 1676, 1451, 1158, 752 cm$^{-1}$. HRMS (ESI): calculated for $C_{17}H_{16}N_2O_3S_1Cl_1$ $[M+H]^+$ requires m/z 363.05702, found m/z 363.05640.

N-[(4-bromo-1H-indol-3-yl)methyl]-4-methylbenzenesulfonamide (5). The title compound was prepared according to the general procedure. Brown solid (16 mg, 34%): m.p. 117-122° C.; purification (hexanes:EtOAc, 60:40), $R_f$=0.22. $^1$H NMR (400 MHz, $CDCl_3$): δ=8.21 (bs, 1H), 7.64 (d, J=8.2 Hz, 2H), 7.23 (dd, J=8.2 Hz, J=0.8 Hz, 1H), 7.20 (dd, J=8.2 Hz, J=0.8 Hz, 1H), 7.15-7.12 (m, 3H), 6.98 (t, J=7.8 Hz, 1H), 4.99 (bt, J=5.9 Hz, 1H), 4.49 (d, J=5.9 Hz, 2H), 2.34 (s, 3H) ppm. $^{13}$C NMR (100 MHz, $CDCl_3$): δ=142.9, 137.5, 137.2, 129.2, 126.9, 126.0, 124.9, 124.0, 123.2, 113.1, 111.5, 110.8, 39.3, 21.4 ppm. IR (neat): v=3326, 2916, 2848, 1639, 1511, 1387, 1294, 1151, 731 cm$^{-1}$. HRMS (ESI): calculated for $C_{16}H_{16}N_2O_2S_1Br_1$ $[M+H]^+$ requires m z 379.01159, found m/z 379.01059.

N-[(7-methyl-1H-indol-3-yl)methyl]benzenesulfonamide (6). The title compound was prepared according to the general procedure. Off-white solid (23 mg, 58%): m.p. 176-179° C.; purification (hexanes: EtOAc, 60:40), $R_f$=0.38. $^1$H NMR (400 MHz, $CDCl_3$): δ=8.02 (bs, 1H), 7.77 (d, J=8.2 Hz, 2H), 7.30 (d, J=8.2 Hz, 2H), 7.23 (t, J=4.5 Hz, 1H), 7.04 (d, J=2.3 Hz, 1H), 7.00 (d, J=5.5 Hz, 2H), 4.55 (bt, J=5.5 Hz, 1H), 4.30 (d, J=5.5 Hz, 2H), 2.45 (s, 3H), 2.44 (s, 3H) ppm. $^{13}$C NMR (100 MHz, $CDCl_3$): δ=143.4, 136.7, 135.8, 129.7, 127.3, 126.5, 125.7, 123.1, 120.5, 120.2, 116.3, 111.4, 39.1, 21.5, 16.6 ppm. IR (neat): v=3386, 3269, 3053, 2917, 1597, 1412, 1300, 1153, 1091, 1041, 909, 810, 736, 668, 540 $cm^{-1}$. HRMS (ESI): calculated for $C_{17}H_{19}N_2O_2S_1$ $[M+H]^+$ requires m/z 315.11673, found m/z 315.10825.

N-[(4-methyl-1H-indol-3-yl)methyl]benzenesulfonamide (7). The title compound was prepared according to the general procedure. Brown solid (24 mg, 63%): m.p. 130-136° C.; purification (hexanes:EtOAc, 60:40), $R_f$=0.34. $^1$H NMR (400 MHz, $CDCl_3$): δ=8.06 (bs, 1H), 7.92-7.88 (m, 2H), 7.62-7.56 (m, 1H), 7.55-7.48 (m, 2H), 7.16 (d, J=7.8 Hz, 1H), 7.07 (t, J=7.4 Hz, 1H), 6.98 (d, J=2.7 Hz, 1H), 6.86-6.82 (m, 1H), 4.51 (m, 1H), 4.41 (d, J=5.1 Hz, 2H), 2.54 (s, 3H) ppm. $^{13}$C NMR (100 MHz, $CDCl_3$): δ=141.9, 139.6, 136.7, 132.6, 130.4, 129.1, 127.2, 126.4, 124.9, 122.6, 121.5, 111.1, 109.3, 40.4, 19.7 ppm. IR (neat): v=3271, 1701, 1446, 1413, 1310, 1154, 1090, 1028, 747, 686 $cm^{-1}$. HRMS (ESI): calculated for $C_{16}H_{17}N_2O_2S_1$ $[M+H]^+$ requires m z 301.10108, found m/z 301.09982.

4-methyl-N-[(1-methyl-1H-indazol-3-yl)methyl]benzenesulfonamide (8). The title compound was prepared according to the general procedure. White solid (26 mg, 66%): m.p. 129-131° C.; purification (hexanes:EtOAc, 60:40), $R_f$=0.26. $^1$H NMR (400 MHz, $CDCl_3$): δ=7.74 (dt, J=8.2 Hz, J=2.0 (×2) Hz, 2H), 7.66 (dt, J=8.2 Hz, J=1.0 Hz, 1H), 7.38 (ddd, J=8.2 Hz, J=6.7 Hz, J=0.8 Hz, 1H), 7.29 (dt, J=8.2 Hz, J=0.8 Hz, 1H), 7.25-7.22 (m, 2H), 7.12 (ddd, J=8.0 Hz, J=6.7 Hz, J=0.8 Hz, 1H), 5.14 (bt, J=5.9 Hz, 1H), 4.47 (d, J=5.9 Hz, 2H), 3.93 (s, 3H), 2.39 (s, 3H) ppm. $^{13}$C NMR (100 MHz, $CDCl_3$): δ=143.4, 140.9, 139.2, 136.5, 129.6, 127.2, 126.7, 121.7, 120.6, 120.2, 109.0, 40.1, 35.3, 21.5 ppm IR (neat): v=3087, 2868, 1599, 1441, 1322, 1153, 1078, 1048, 800, 656 $cm^{-1}$. HRMS (ESI): calculated for $C_{16}H_{18}N_3O_2S_1$ $[M+H]^+$ requires m z 316.11197, found m/z 316.11053.

4-methyl-N-[(1-methyl-1H-indazol-5-yl)methyl]benzenesulfonamide (9). The title compound was prepared according to the general procedure. White solid (26 mg, 60%): m.p. 147-150° C.; purification (hexanes:EtOAc, 60:40), $R_f$=0.21. $^1$H NMR (400 MHz, $CDCl_3$): δ=7.88 (s, 1H), 7.77 (dt, J=8.2 Hz, J=2.0 (×2) Hz, 2H), 7.50 (s, 1H), 7.33-7.24 (m, 4H), 4.74 (bt, J=5.9 Hz, 1H), 4.22 (d, J=5.9 Hz, 2H), 4.05 (s, 3H), 2.43 (s, 3H) ppm. $^{13}$C NMR (100 MHz, $CDCl_3$): δ=143.5, 139.5, 136.9, 132.6, 129.7, 128.4, 127.2, 126.7, 123.9, 120.4, 109.4, 47.5, 35.6, 21.5 ppm. IR (neat): v=3166, 2931, 1512, 1327, 1156, 1055, 800, 750, 660 $cm^{-1}$. HRMS (ESI): calculated for $C_{16}H_{18}N_3O_2S_1$ $[M+H]^+$ requires m/z 316.11197, found m/z 316.11096.

4-chloro-N-[(1-methyl-1H-indazol-5-yl)methyl]benzenesulfonamide (10). The title compound was prepared according to the general procedure. White solid (15 mg, 36%): m.p. 148-150° C.; purification (hexanes: EtOAc, 60:40), $R_f$=0.19. $^1$H NMR (400 MHz, $CDCl_3$): δ=7.91 (d, J=0.8 Hz, 1H), 7.79 (dt, J=8.6 Hz, J=2.0 (×2) Hz, 2H), 7.53-7.51 (m, 1H), 7.45 (dt, J=8.6 Hz, J=2.0 (×2) Hz, 2H), 7.31 (d, J=8.6 Hz, 1H), 7.23 (dd, J=8.6 Hz, J=1.6 Hz, 1H), 4.69 (bt, J=6.3 Hz, 1H), 4.26 (d, J=6.3 Hz, 2H), 4.06 (s, 3H) ppm. $^{13}$C NMR (100 MHz, $CDCl_3$): δ=139.5, 139.2, 138.6, 132.7, 129.4, 128.6, 128.0, 126.5, 123.9, 120.5, 109.5, 47.6, 35.7 ppm. IR (neat): v=3300, 2923, 2851, 1514, 1326, 1150, 1091, 817, 750, 620 $cm^{-1}$. HRMS (ESI): calculated for $C_{15}H_{15}N_3O_2S_1Cl_1$ $[M+H]^+$ requires m/z 336.05735, found m/z 336.05640.

4-chloro-N-[(1-methyl-1H-pyrazol-4-yl)methyl]benzenesulfonamide (11). The title compound was prepared according to the general procedure. White solid (19 mg, 51%): m.p. 125-127° C.; purification (hexanes: EtOAc, 60:40), $R_f$=0.06. $^1$H NMR (400 MHz, $CDCl_3$): δ=7.78 (dt, J=8.6 Hz, J=2.0 (×2) Hz, 2H), 7.48 (dt, J=8.6 Hz, J=2.0 (×2) Hz, 2H), 7.24 (s, 1H), 7.20 (s, 1H), 4.90 (bt, J=5.5 Hz, 1H), 4.03 (d, J=5.5 Hz, 2H), 3.81 (s, 3H). $^{13}$C NMR (100 MHz, $CDCl_3$): δ=139.2, 138.6, 138.5, 129.5, 129.4, 128.6, 116.7, 39.0, 37.8 ppm. IR (neat): v=3148, 3054, 2936, 2856, 2782, 1741, 1585, 1566, 1473, 1340, 1159, 1059, 997, 846, 758, 612 $cm^{-1}$. HRMS (ESI): calculated for $C_{11}H_{13}Cl_1N_3O_2S_1$ $[M+H]^+$ requires m/z 286.04170, found m/z 286.03979.

N-[(2-methoxypyridin-3-yl)methyl]-4-methylbenzenesulfonamide (12). The title compound was prepared according to the general procedure. Additional purification (after column chromatography) included dissolving the mixture of product amine and sulfonamide starting material in 5 mL of EtOAc along with 5 mL of 5M HCl in a separatory funnel. The aqueous acid (containing the protonated pyridinium product) was separated from the organic and basified with approximately 3-4 mL of 50% w/w NaOH solution. The deprotonated product was then extracted from the aqueous portion with EtOAc (3×5 mL), dried with $Na_2SO_4$, and the solvent was removed under vacuum. White solid (13 mg, 36%): m.p. 95-96° C.; purification (hexanes:EtOAc, 50:50), $R_f$=0.66. $^1$H NMR (400 MHz, $CDCl_3$): δ=8.01 (dd, J=5.1 Hz, J=2.0 Hz, 1H), 7.64 (dt, J=8.2 Hz, J=2.0 (×2) Hz, 2H), 7.37 (dd, J=7.4 Hz, J=2.0 Hz, 1H), 7.21 (d, J=7.8 Hz, 2H), 6.74 (dd, J=7.0 Hz, J=5.1 Hz, 1H), 5.15 (t, J=6.7 Hz, 1H), 4.11 (d, J=6.7 Hz, 2H), 3.88 (s, 3H), 2.39 (s, 3H) ppm. $^{13}$C NMR (100 MHz, $CDCl_3$): δ=161.4, 146.2, 143.3, 137.8, 137.2, 129.5, 127.0, 118.9, 116.7, 53.4, 43.2, 21.5 ppm. IR (neat): v=3275, 2951, 1596, 1466, 1412, 1321, 1153, 1092, 1018, 812, 776, 660 $cm^{-1}$. HRMS (ESI): calculated for $C_{14}H_{17}N_2O_3S_1$ $[M+H]^+$ requires m/z 293.09599, found m/z 293.09415.

N-[(2-methoxypyridin-3-yl)methyl]benzenesulfonamide (13). The title compound was prepared according to the general procedure. Additional purification (after column chromatography) included dissolving the mixture of product amine and sulfonamide starting material in 5 mL of EtOAc along with 5 mL of 5M HCl in a separatory funnel. The aqueous acid (containing the protonated pyridinium product) was separated from the organic and basified with approximately 3-4 mL of 50% w/w NaOH solution. The deprotonated product was then extracted from the aqueous portion with EtOAc (3×5 mL), dried with $Na_2SO_4$, and the solvent was removed under vacuum. White solid (12 mg, 32%): m.p. 116-118° C.; purification (hexanes: EtOAc, 50:50), $R_f$=0.47. $^1$H NMR (400 MHz, $CDCl_3$): δ=7.97 (d, J=5.1 Hz, 1H), 7.75 (m, 2H), 7.42-7.34 (m, 3H), 6.71 (dd, J=7.0 Hz, 5.1 Hz, 1H), 5.40 (bs, 1H), 4.12 (d, J=6.3 Hz, 2H), 3.84 (s, 3H) ppm. $^{13}$C NMR (100 MHz, $CDCl_3$): δ=161.3, 146.2, 140.1, 137.7, 132.5, 128.8, 126.8, 118.7, 116.7, 53.3, 43.1 ppm. IR (neat): v=3057, 2917, 2850, 1601, 1589, 1468, 1411, 1363, 1334, 1250, 1158, 1080, 1012, 105, 749, 693, 579, 528 $cm^{-1}$. HRMS (ESI): calculated for $C_{13}H_{15}N_2O_3S_1$ $[M+H]c^+$ requires m/z 279.08034, found m/z 279.07294.

4-chloro-N-(pyrimidin-5-ylmethyl)benzenesulfonamide (14). The title compound was prepared according to the general procedure. White solid (9 mg, 26%): m.p. 154-160° C.; purification (100% EtOAc), $R_f$=0.46; $^1$H NMR (400 MHz, $CDCl_3$): δ=9.14 (s, 1H), 8.64 (s, 2H), 7.79 (dt, J=8.2 Hz, J=2.7 (×2) Hz, 2H), 7.51 (dt, J=8.2 Hz, J=2.7 (×2) Hz, 2H), 5.01 (bs, 1H), 4.22 (s, 2H) ppm. $^{13}$C NMR (100 MHz, $CDCl_3$): δ=158.3, 156.5, 139.8, 138.0, 130.0, 129.7, 128.5, 42.5 ppm. IR (neat): v=3047, 2852, 1567, 1411, 1321, 1155, 822, 722, 608 cm$^{-1}$. HRMS (ESI): calculated for $C_{11}H_{11}N_3O_2S_1Cl_1$ [M+H]$^+$ requires m/z 284.02605, found m/z 284.02499.

N-(pyrimidin-5-ylmethyl)benzenesulfonamide (15). The title compound was prepared according to the general procedure. White solid (8 mg, 26%): m.p. 54-60° C.; purification (100% EtOAc), $R_f$=0.34. $^1$H NMR (400 MHz, $CDCl_3$): δ=9.11 (s, 1H), 8.62 (s, 2H), 7.88-7.84 (m, 2H), 7.64-7.59 (m, 1H), 7.56-7.51 (m, 2H), 5.11 (bs, 1H), 4.22 (s, 2H) ppm. $^{13}$C NMR (100 MHz, $CDCl_3$): δ=158.3, 156.4, 139.5, 133.2, 130.1, 129.4, 127.0, 42.5 ppm. IR (neat): ν=3084, 2876, 1675, 1569, 1445, 1410, 1313, 1154, 1074, 1043, 688 cm$^{-1}$. HRMS (ESI): calculated for $C_{11}H_{12}N_3O_2S_1$ [M+H]$^+$ requires m z 250.06502, found m/z 250.06349.

4-methyl-N-(pyrazin-2-ylmethyl)benzenesulfonamide (16). The title compound was prepared according to the general procedure. White solid (14 mg, 42%): m.p. 87-92° C.; purification (100% EtOAc), $R_f$=0.54. $^1$H NMR (400 MHz, $CDCl_3$): δ=8.50-8.41 (m, 3H), 7.74 (d, J=8.2 Hz, 2H), 7.26 (d, J=8.2 Hz, 2H), 5.56 (bt, J=5.5 Hz, 1H), 4.32 (d, J=5.5 Hz, 2H), 2.40 (s, 3H) ppm. $^{13}$C NMR (100 MHz, $CDCl_3$): δ=143.9, 143.8, 143.7, 143.6, 136.4, 129.8, 129.7, 127.2, 45.5, 21.5 ppm. IR (neat): ν=3130, 2916, 1599, 1458, 1406, 1329, 1187, 1091, 1018, 870, 816, 707, 663 cm$^{-1}$. HRMS (ESI): calculated for $C_{12}H_{14}N_3O_2S_1$ [M+H]$^+$ requires m/z 264.08067, found m/z 264.07947.

4-methyl-N-(1,3-thiazol-4-ylmethyl)benzenesulfonamide (17). The title compound was prepared according to the general procedure. White solid (15 mg, 44%): m.p. 119-122° C.; purification (hexanes:EtOAc, 60:40), $R_f$=0.18. $^1$H NMR (400 MHz, $CDCl_3$): δ=8.68 (d, J=2.0 Hz, 1H), 7.67 (dt, J=8.2 Hz, J=2.0 (×2) Hz, 2H), 7.25-7.21 (m, 2H), 7.11-7.09 (m, 1H), 5.65 (bt, J=6.3 Hz, 1H), 4.32 (d, J=6.3 Hz, 2H), 2.39 (s, 3H) ppm. $^{13}$C NMR (100 MHz, $CDCl_3$): δ=153.6, 152.3, 143.4, 136.9, 129.6, 127.1, 115.7, 42.9, 21.5 ppm. IR (neat): ν=3070, 2863, 1600, 1458, 1412, 1314, 1258, 1146, 1093, 1072, 812, 730, 662 cm$^{-1}$. HRMS (ESI): calculated for $C_{11}H_{13}N_2O_2S_2$ [M+H]$^+$ requires m/z 269.04185, found m/z 269.04280.

4-chloro-N-(1,3-thiazol-4-ylmethyl)benzenesulfonamide (18). The title compound was prepared according to the general procedure. White solid (13 mg, 35%): m.p. 130-132° C.; purification (100% EtOAc), $R_f$=0.86. $^1$H NMR (400 MHz, $CDCl_3$): δ=8.68 (d, J=2.3 Hz, 1H), 7.70 (dt, J=9.0 Hz, J=2.4 (×2) Hz, 2H), 7.39 (dt, J=9.0 Hz, J=2.4 (×2) Hz, 2H), 7.10 (m, 1H), 5.82 (bt, J=6.3 Hz, 1H), 4.35 (d, J=6.3 Hz, 2H) ppm. $^{13}$C NMR (100 MHz, $CDCl_3$): δ=153.8, 152.0, 139.0, 138.5, 129.2, 128.5, 116.0, 42.9 ppm. IR (neat): ν=3257, 3109, 1586, 1476, 1325, 1313, 1278, 1158, 1092, 1047, 933, 878, 828, 756, 662, 615, 507 cm$^{-1}$. HRMS (ESI): calculated for $C_{10}H_{10}Cl_1N_2O_2S_2$ [M+H]$^+$ requires m/z 288.98722, found m/z 288.97977.

4-methyl-N-(1,3-thiazol-2-ylmethyl)benzenesulfonamide (19). The title compound was prepared according to the general procedure. Off-white oil (17 mg, 51%): purification (hexanes:EtOAc, 60:40), $R_f$=0.15. $^1$H NMR (400 MHz, $CDCl_3$): δ=7.76 (dt, J=8.2 Hz, J=2.0 (×2) Hz, 2H), 7.65 (d, J=3.1 Hz, 1H), 7.31-7.25 (m, 3H), 5.56 (bt, J=6.3 Hz, 1H), 4.48 (d, J=6.3 Hz, 2H), 2.42 (s, 3H) ppm. $^{13}$C NMR (100 MHz, $CDCl_3$): δ=165.9, 143.8, 142.5, 136.5, 129.8, 127.2, 119.9, 44.4, 21.5 ppm. IR (neat): ν=3084, 2850, 1504, 1329, 1159, 1090, 1058, 736, 658 cm$^{-1}$. HRMS (ESI): calculated for $C_{11}H_{13}N_2O_2S_2$ [M+H]$^+$ requires m/z 269.04185, found m/z 269.04013.

4-chloro-N-(furan-2-ylmethyl)benzenesulfonamide (20). The title compound was prepared according to the general procedure. White solid (18 mg, 52%): m.p. 118-120° C.; purification (hexanes:EtOAc, 60:40), $R_f$=0.65. $^1$H NMR (400 MHz, $CDCl_3$): δ=7.75 (dt, J=9.0 Hz, J=2.4 (×2) Hz, 2H), 7.44 (dt, J=9.0 Hz, J=2.4 (×2) Hz, 2H), 7.23 (m, 1H), 6.22 (dd, J=3.3 Hz, J=1.8 Hz, 1H), 6.10 (m, 1H), 4.79 (bt, J=5.9 Hz, 1H), 4.22 (d, J=5.9 Hz, 2H) ppm. $^{13}$C NMR (100 MHz, $CDCl_3$): δ=149.1, 142.6, 139.1, 138.5, 129.2, 128.5, 110.4, 108.5, 40.1 ppm. IR (neat): ν=3260, 1586, 1476, 1433, 1320, 1158, 1148, 1091, 1012, 922, 881, 824, 724 cm$^{-1}$. HRMS (ESI): calculated for $C_{11}H_{11}N_1O_3S_1Cl_1$ [M+H]$^+$ requires m/z 272.01482, found m/z 272.01401.

4-methyl-N-[(2-methyl-1,3-oxazol-4-yl)methyl]benzenesulfonamide (21). The title compound was prepared according to the general procedure. White solid (19 mg, 57%): m.p. 156-158° C.; purification (hexanes:EtOAc, 60:40), $R_f$=0.06. $^1$H NMR (400 MHz, $CDCl_3$): δ=7.71 (dt, J=8.2 Hz, J=2.0 (×2) Hz, 2H), 7.31 (t, J=1.2 Hz, 1H), 7.27 (d, J=8.2 Hz, 2H), 5.14 (bt, J=6.3 Hz, 1H), 4.03 (dd, J=6.3 Hz, J=1.2 Hz, 2H), 2.42 (s, 3H), 2.35 (s, 3H) ppm. $^{13}$C NMR (100 MHz, $CDCl_3$): δ=162.0, 143.5, 136.7, 135.9, 135.2, 129.6, 127.2, 39.1, 21.5, 13.7 ppm. IR (neat): ν=3102, 2959, 2928, 2873, 1725, 1578, 1461, 1322, 1275, 1153, 1072, 930, 766, 660 cm$^{-1}$. HRMS (ESI): calculated for $C_{12}H_{15}N_2O_3S_1$ [M+H]$^+$ requires m/z 267.08034, found m/z 267.07907.

4-methyl-N-(quinolin-6-ylmethyl)benzenesulfonamide (22). The title compound was prepared according to the general procedure. White solid (12 mg, 31%). m.p. 148-150° C. Purification (EtOAc). $R_f$=0.51. $^1$H NMR (400 MHz, $CDCl_3$): δ=8.90 (dd, J=4.1 Hz, J=1.8 Hz, 1H), 8.07 (dd, J=7.8 Hz, J=1.2 Hz, 1H), 8.01 (d, J=8.6 Hz, 1H), 7.77 (m, 2H), 7.65 (d, J=1.2 Hz, 1H), 7.52, (dd, J=8.6 Hz, J=2.2 Hz, 1H), 7.40 (dd, J=8.6 Hz, J=4.1 Hz, 1H), 7.29 (m, 2H), 4.84 (bt, J=6.3 Hz, 1H), 4.34 (d, J=6.3 Hz, 2H), 2.41 (s, 3H) ppm. $^{13}$C NMR (100 MHz, $CDCl_3$) δ 150.6, 147.7, 143.7, 136.9, 135.9, 134.7, 129.9, 129.8, 129.2, 128.0, 127.2, 126.4, 121.5, 47.0, 21.5 ppm. IR (neat): ν=3097, 2924, 2841, 1595, 1313, 1152, 885, 837, 658, 540 cm$^{-1}$. HRMS (ESI): calculated for $C_{17}H_{17}N_2S_1O_2$ [M+H]$^+$ requires m/z 313.10108, found m/z 313.10080.

N-(1H-indol-3-ylmethyl)-4-methoxybenzenesulfonamide (23). The title compound was prepared according to the general procedure. Pale yellow solid (25 mg, 63%). m.p. 170-173° C. Purification (hexanes: EtOAc, 50:50). $R_f$=0.43. $^1$H NMR (400 MHz, $(CD_3)_2CO$) δ=10.08 (bs, 1H), 7.84 (dt, J=8.6 Hz, J=3.1 Hz, 2H), 7.51 (d, J=7.8 Hz, 1H), 7.36 (d, J=7.8 Hz, 1H), 7.18 (d, J=2.0 Hz, 1H), 7.09 (m, 3H), 6.99 (m, 1H), 6.42 (bt, J=6.3 (×2) Hz, 1H), 4.26 (d, J=6.3 Hz, 2H), 3.90 (s, 3H) ppm. $^{13}$C NMR (100 MHz, $(CD_3)_2CO$): δ=163.5, 137.7, 133.7, 130.0, 127.7, 124.8, 122.4, 119.8, 119.6, 114.9, 112.2, 111.8, 56.0, 39.6 ppm. IR (neat): ν=3385, 3290, 3003, 2837, 1594, 1261, 1154, 1022, 538 cm$^{-1}$. HRMS (ESI): calculated for $C_{16}H_{16}N_2S_1O_3$ [M+Na]$^+$ requires m z 339.07794, found m/z 339.07790.

N-(1H-indol-3-ylmethyl)-4-(trifluoromethyl)benzenesulfonamide (24). The title compound was prepared according to the general procedure. White solid (18 mg, 41%). m.p. 199-201° C. Purification (hexanes: EtOAc, 60:40). $R_f$=0.37. $^1$H NMR (400 MHz, $(CD_3)_2CO$): δ=10.08 (bs, 1H), 8.01 (d, J=8.6 Hz, 2H), 7.79 (d, J=8.2 Hz, 2H), 7.49 (d, J=7.8 Hz, 1H), 7.31 (dd, J=8.2 Hz, J=0.78 Hz, 1H), 7.19 (d, J=1.6 Hz, 1H), 7.08 (t, J=7.6 (×2) Hz, 1H), 6.97 (m, 2H), 4.38 (d, J=5.9 Hz, 2H) ppm. $^{13}$C NMR (100 MHz, $(CD_3)_2CO$): δ 146.0, 137.6, 133.7, 133.4, 128.5, 127.5, 126.6, 125.2, 122.5, 119.8, 119.4, 112.2, 111.4, 39.7 ppm. IR (neat): ν=3394, 3312, 1404, 1358, 1158, 846, 744 cm$^{-1}$. HRMS (ESI): calculated for $C_{16}H_{13}N_2S_1O_2F_3$ [M+Na]$^+$ requires m/z 377.05475, found m/z 377.05430.

N-(1H-indol-3-ylmethyl)-3-nitrobenzenesulfonamide (25). The title compound was prepared according to the general procedure. Yellow solid (8 mg, 19%). m.p. 182-184° C. Purification (hexanes: EtOAc, 50:50). $R_f$=0.46. $^1$H NMR (400 MHz, $(CD_3)_2CO$): δ=10.05 (bs, 1H), 8.40 (m, 1H), 8.20 (dt, J=8.2 Hz, J=0.78 Hz, 1H), 8.05 (dt, J=7.8 Hz, J=0.78 Hz, 1H), 7.60 (t, J=8.0 (×2) Hz, 1H), 7.48 (d, J=7.8 Hz, 1H), 7.26-7.17 (m, 3H), 7.01 (t, J=7.6 (×2) Hz, 1H), 6.90 (m, 1H), 4.43 (d, J=5.9 Hz, 2H) ppm. $^{13}$C NMR (100 MHz, $(CD_3)_2CO$): δ=144.0, 137.5, 133.2, 130.8, 127.3, 126.8, 125.5, 125.3, 122.5, 122.4, 119.8, 119.4, 112.0, 111.3, 39.7 ppm. IR (neat): v=3386, 3303, 3105, 2923, 1522, 1346, 1159, 748 cm$^{-1}$. HRMS (ESI): calculated for $C_{15}H_{14}N_3S_1O_4$ [M+Na]$^+$ requires m/z 354.05245, found m/z 354.05190.

N-(1H-indol-3-ylmethyl)methanesulfonamide (26). The title compound was prepared according to the general procedure. Brown solid (9 mg, 34%). m.p. 133-135° C. Purification (hexanes: EtOAc, 50:50). $R_f$=0.28. $^1$H NMR (400 MHz, $(CD_3)_2CO$): δ=10.20 (bs, 1H), 7.73 (d, J=7.8 Hz, 1H), 7.42 (d, J=7.8 Hz, 1H), 7.36 (d, J=2.0 Hz, 1H), 7.13 (t, J=7.4 (×2) Hz, 1H), 7.06 (t, J=7.4 (×2) Hz, 1H), 6.20 (bs, 1H), 4.49 (d, J=5.9 Hz, 2H), 2.82 (s, 3H) ppm. $^{13}$C NMR (100 MHz, $(CD_3)_2CO$): δ=137.8, 127.7, 124.9, 122.5, 119.9, 119.6, 112.4, 112.3, 40.3, 39.5 ppm. IR (neat): v=3394, 3270, 3016, 2929, 2527, 1140, 738, 505, 428 cm$^{-1}$. HRMS (ESI): calculated for $C_{10}H_{12}N_2S_1O_2$ [M+Na]$^+$ requires m/z 247.05172, found m/z 247.05120.

N-[(4-bromo-1H-indol-3-yl)methyl]-4-chlorobenzenesulfonamide (27). The title compound was prepared according to the general procedure. White solid (7 mg, 25%). M.p. 186-188° C. Purification (hexanes: EtOAc, 50:50). $R_f$=0.53. $^1$H NMR (400 MHz, $(CD_3)_2CO$) δ=10.48 (bs, 1H), 7.83 (dt, $J_1$=8.6 Hz, $J_2$=2.3 Hz, 2H), 7.51 (dt, $J_1$=8.2 Hz, $J_2$=2.3 Hz, 2H), 7.38 (d, $J_1$=8.2 Hz, 1H), 7.34 (d, $J_1$=1.6 Hz, 1H), 7.16 (d, $J_1$=7.4 Hz, 1H), 6.98 (t, $J_1$=7.4×(2) Hz, 1H), 6.61 (t, $J_1$=5.5×(2) Hz, 1H), 4.55 (d, $J_1$=5.1 Hz, 2H) ppm. $^{13}$C NMR (100 MHz, $(CD_3)_2CO$) δ 140.2, 138.1, 128.8, 128.72, 128.70, 126.9, 124.9, 123.2, 122.5, 112.9, 111.12, 111.07, 39.1 ppm. IR (neat): v=3355, 1704, 1334, 1189, 1092, 747 cm$^{-1}$. HRMS (ESI): calculated for $C_{15}H_{11}BrClN_2O_2S$ [M−H]$^+$ requires m/z 396.94131, found m/z 396.94183.

4-chloro-N-[(7-methyl-1H-indol-3-yl)methyl]benzenesulfonamide (28). The title compound was prepared according to the general procedure. Tan solid (17 mg, 42%). M.p. 204-206° C. Purification (hexanes: EtOAc, 50:50). $R_f$=0.59. $^1$H NMR (400 MHz, $(CD_3)_2CO$) δ=10.06 (bs, 1H), 7.81 (dt, $J_1$=9.0 Hz, $J_2$=2.3 Hz, 2H), 7.51 (dt, $J_1$=10.2 Hz, $J_2$=3.1 Hz, 2H), 7.34 (t, $J_1$=4.5×(2) Hz, 1H), 7.16 (d, $J_1$=2.0 Hz, 1H), 6.90 (d, $J_1$=4.7 Hz, 2H), 6.76 (t, $J_1$=4.7×(2) Hz, 1H), 4.32 (d, $J_1$=5.9 Hz, 2H), 2.45 (s, 3H) ppm. $^{13}$C NMR (100 MHz, $(CD_3)_2CO$) δ 140.1, 137.4, 136.2, 128.7, 128.6, 126.3, 123.8, 122.1, 120.5, 119.2, 116.3, 111.0, 38.9, 15.9 ppm. IR (neat): v=3402, 3282, 3093, 2917, 1318, 1158, 1093, 1024, 484 cm$^{-1}$. HRMS (ESI): calculated for $C_{16}H_{14}ClN2O_2S$ [M−H]$^+$ requires m/z 333.04645, found m/z 333.04688.

4-chloro-N-[(1-methyl-1H-indol-3-yl)methyl]benzenesulfonamide (29). The title compound was prepared according to the general procedure. White solid (14 mg, 32%). m.p. 184-187° C. Purification (hexanes: EtOAc, 50:50). $R_f$=0.70. $^1$H NMR (400 MHz, $CDCl_3$): δ=7.75 (dt, J=9.4 Hz, J=2.7 Hz, 2H), 7.43-7.36 (m, 3H), 7.28-7.21 (m, 2H), 7.08 (ddd, J=8.0 Hz, J=6.5 Hz, J=1.6 Hz, 1H), 6.86 (s, 1H), 4.61 (bt, J=5.5 (×2) Hz, 1H), 4.33 (d, J=5.5 Hz, 2H), 3.70 (s, 3H) ppm. $^{13}$C NMR (100 MHz, $CDCl_3$): δ=138.9, 138.5, 137.1, 129.1, 128.6, 128.1, 126.5, 122.3, 119.7, 118.5, 109.5, 108.9, 38.9, 32.7 ppm. IR (neat): v=3303, 3058, 1473, 1311, 1157, 1041, 826, 736, 544 cm$^{-1}$. HRMS (ESI): calculated for $C_{16}H_{15}N_2S_1O_2Cl_1$ [M+Na]$^+$ requires m/z 357.04405, found m/z 357.04210.

4-chloro-N-[(4-methyl-1H-indol-3-yl)methyl]benzenesulfonamide (30). The title compound was prepared according to the general procedure. Tan solid (16 mg, 37%). m.p. 160-162° C. Purification (hexanes: EtOAc, 60:40). $R_f$=0.43. $^1$H NMR (400 MHz, $(CD_3)_2C_0$): δ=10.12 (bs, 1H), 7.91 (dt, J=9.0 Hz, J=2.0 Hz, 2H), 7.61 (dt, J=9.0 Hz, J=2.0 Hz, 2H), 7.18 (d, J=8.2 Hz, 1H), 7.15 (d, J=2.3 Hz, 1H), 6.96 (dd, J=8.2, J=7.0 Hz, 1H), 6.74 (dt, J=7.0 Hz, J=1.0 (×2) 1H), 6.62 (bt, J=5.5 Hz, 1H), 4.38 (d, J=5.5 Hz, 2H), 2.57 (s, 3H) ppm. $^{13}$C NMR (100 MHz, $(CD_3)_2CO$): δ=140.7, 138.6, 138.1, 130.9, 129.9, 129.7, 126.3, 126.0, 122.6, 121.5, 111.6, 110.2, 41.2, 20.1 ppm. IR (neat): v=3390, 3273, 2923, 1336, 1150, 1093, 752 cm$^1$. HRMS (ESI): calculated for $C_{16}H_{16}Cl_1N_2O_2S_1$ [M+H]$^+$ requires m/z 335.0621, found m/z 335.0610.

In addition to the foregoing N-benzyl sulfonamides, the following compounds have also been generated using the methods discussed above. Each of the foregoing and following compounds are depicted in FIG. 7 as identified by the number in parentheses following the name of the compound.

4-methyl-N-[(2-methyl-1H-indol-3-yl)methyl]benzenesulfonamide (31)
4-chloro-N-[(2-methyl-1H-indol-3-yl)methyl]benzenesulfonamide (32)
4-chloro-N-[(2-chloro-1H-indol-3-yl)methyl]benzenesulfonamide (33)
4-chloro-N-[(5-methoxy-1H-indol-3-yl)methyl]benzenesulfonamide (34)
4-chloro-N-[(5-fluoro-1H-indol-3-yl)methyl]benzenesulfonamide (35)
4-chloro-N-[(5-nitro-1H-indol-3-yl)methyl]benzenesulfonamide (36)
4-fluoro-N-(1H-indol-3-ylmethyl)benzenesulfonamide (37)
4-bromo-N-(1H-indol-3-ylmethyl)benzenesulfonamide (38)
4-chloro-N-(quinolin-6-ylmethyl)benzenesulfonamide (39)
3-bromo-N-(1H-indol-3-ylmethyl)benzenesulfonamide (40)
4-chloro-N-(1H-indol-4-ylmethyl)benzenesulfonamide (41)
4-chloro-N-(1H-indol-5-ylmethyl)benzenesulfonamide (42)
4-chloro-N-(1H-indol-6-ylmethyl)benzenesulfonamide (43)
4-chloro-N-{[1-(phenylsulfonyl)-1H-indol-2-yl]methyl}benzenesulfonamide (44)
3-chloro-N-(1H-indol-3-ylmethyl)benzenesulfonamide (45)
3-fluoro-N-(1H-indol-3-ylmethyl)benzenesulfonamide (46)
2-fluoro-N-(1H-indol-3-ylmethyl)benzenesulfonamide (47)
2-bromo-N-(1H-indol-3-ylmethyl)benzenesulfonamide (48)
N-(1H-indol-3-ylmethyl)-2-methylbenzenesulfonamide (49)
3,5-dichloro-N-(1H-indol-3-ylmethyl)benzenesulfonamide (50)
3,5-difluoro-N-(1H-indol-3-ylmethyl)benzenesulfonamide (51)
2,3-dichloro-N-(1H-indol-3-ylmethyl)benzenesulfonamide (52)
2,4-difluoro-N-(1H-indol-3-ylmethyl)benzenesulfonamide (53)
N-(1H-indol-3-ylmethyl)-2-nitrobenzenesulfonamide (54)
N-(1H-indol-6-ylmethyl)pyridine-3-sulfonamide (55)
N-(1H-indol-6-ylmethyl)biphenyl-4-sulfonamide (56)
5-chloro-N-(1H-indol-6-ylmethyl)thiophene-2-sulfonamide (57)
N-(1H-indol-5-ylmethyl)-4-methylbenzenesulfonamide (58)
4-bromo-N-(1H-indol-6-ylmethyl)benzenesulfonamide (59)

N-(1H-indol-6-ylmethyl)-4-methoxybenzenesulfonamide (60)
N-(1H-indol-6-ylmethyl)-4-phenoxybenzenesulfonamide (61)
4-fluoro-N-(1H-indol-6-ylmethyl)benzenesulfonamide (62)
N-(1H-indol-6-ylmethyl)-4-nitrobenzenesulfonamide (63)
N-(1H-indol-6-ylmethyl)-4-(trifluoromethyl)benzenesulfonamide (64)
N-(1H-indol-6-ylmethyl)-4-methylbenzenesulfonamide (65)
3-chloro-N-(1H-indol-6-ylmethyl)benzenesulfonamide (66)
3-fluoro-N-(1H-indol-6-ylmethyl)benzenesulfonamide (67)
N-(1H-indol-6-ylmethyl)-3-(trifluoromethyl)benzenesulfonamide (68)
N-(1H-indol-6-ylmethyl)-3-nitrobenzenesulfonamide (69)
2-chloro-N-(1H-indol-6-ylmethyl)benzenesulfonamide (70)
2-fluoro-N-(1H-indol-6-ylmethyl)benzenesulfonamide (71)
N-(1H-indol-6-ylmethyl)-2-(trifluoromethyl)benzenesulfonamide (72)
N-(1H-indol-6-ylmethyl)-2-nitrobenzenesulfonamide (73)
2,4-dichloro-N-(1H-indol-6-ylmethyl)benzenesulfonamide (74)
3,5-dichloro-N-(1H-indol-6-ylmethyl)benzenesulfonamide (75)
2,6-difluoro-N-(1H-indol-6-ylmethyl)benzenesulfonamide (76)
4-fluoro-N-(1H-indol-6-ylmethyl)-2-methylbenzenesulfonamide (77)
5-fluoro-N-(1H-indol-6-ylmethyl)-2-methylbenzenesulfonamide (78)
N-(1H-indol-6-ylmethyl)thiophene-2-sulfonamide (79)
N-(1H-indol-6-ylmethyl)quinoline-8-sulfonamide (80)
N-(1H-indol-6-ylmethyl)morpholine-4-sulfonamide (81)
4-bromo-N-(1H-indol-5-ylmethyl)benzenesulfonamide (82)
N-(1H-indol-5-ylmethyl)biphenyl-4-sulfonamide (83)
N-(1H-indol-5-ylmethyl)-4-phenoxybenzenesulfonamide (84)
N-(1H-indol-5-ylmethyl)-4-methoxybenzenesulfonamide (85)
N-(1H-indol-5-ylmethyl)-4-nitrobenzenesulfonamide (86)
N-(1H-indol-5-ylmethyl)-4-(trifluoromethyl)benzenesulfonamide (87)
4-fluoro-N-(1H-indol-5-ylmethyl)benzenesulfonamide (88)
N-(1H-indol-5-ylmethyl)-3-nitrobenzenesulfonamide (89)
N-(1H-indol-5-ylmethyl)-3-(trifluoromethyl)benzenesulfonamide (90)
3-fluoro-N-(1H-indol-5-ylmethyl)benzenesulfonamide (91)
3-chloro-N-(1H-indol-5-ylmethyl)benzenesulfonamide (92)
N-(1H-indol-5-ylmethyl)-2-nitrobenzenesulfonamide (93)
N-(1H-indol-5-ylmethyl)-2-(trifluoromethyl)benzenesulfonamide (94)
2-fluoro-N-(1H-indol-5-ylmethyl)benzenesulfonamide (95)
2-chloro-N-(1H-indol-5-ylmethyl)benzenesulfonamide (96)
2,4-dichloro-N-(1H-indol-5-ylmethyl)benzenesulfonamide (97)
3,5-dichloro-N-(1H-indol-5-ylmethyl)benzenesulfonamide (98)
2,6-difluoro-N-(1H-indol-5-ylmethyl)benzenesulfonamide (99)
4-fluoro-N-(1H-indol-5-ylmethyl)-2-methylbenzenesulfonamide (100)
5-fluoro-N-(1H-indol-5-ylmethyl)-2-methylbenzenesulfonamide (101)
N-(1H-indol-5-ylmethyl)thiophene-2-sulfonamide (102)
5-chloro-N-(1H-indol-5-ylmethyl)thiophene-2-sulfonamide (103)
N-(1H-indol-5-ylmethyl)pyridine-3-sulfonamide (104)
N-(1H-indol-5-ylmethyl)quinoline-8-sulfonamide (105)
N-(1H-indol-5-ylmethyl)morpholine-4-sulfonamide (106)
N-(1H-indol-5-ylmethyl)-4-methylpiperidine-1-sulfonamide (107)
N-(1H-indol-4-ylmethyl)-4-methylbenzenesulfonamide (108)
4-bromo-N-(1H-indol-4-ylmethyl)benzenesulfonamide (109)
N-(1H-indol-4-ylmethyl)biphenyl-4-sulfonamide (110)
N-(1H-indol-4-ylmethyl)-4-phenoxybenzenesulfonamide (111)
N-(1H-indol-4-ylmethyl)-4-nitrobenzenesulfonamide (112)
N-(1H-indol-4-ylmethyl)-4-(trifluoromethyl)benzenesulfonamide (113)
N-(1H-indol-4-ylmethyl)-4-methoxybenzenesulfonamide (114)
4-fluoro-N-(1H-indol-4-ylmethyl)benzenesulfonamide (115)
3-fluoro-N-(1H-indol-4-ylmethyl)benzenesulfonamide (116)
N-(1H-indol-4-ylmethyl)-3-(trifluoromethyl)benzenesulfonamide (117)
N-(1H-indol-4-ylmethyl)-3-nitrobenzenesulfonamide (118)
3-chloro-N-(1H-indol-4-ylmethyl)benzenesulfonamide (119)
N-(1H-indol-4-ylmethyl)benzenesulfonamide (120)
2-fluoro-N-(1H-indol-4-ylmethyl)benzenesulfonamide (121)
N-(1H-indol-4-ylmethyl)-2-(trifluoromethyl)benzenesulfonamide (122)
N-(1H-indol-4-ylmethyl)-2-nitrobenzenesulfonamide (123)
2-chloro-N-(1H-indol-4-ylmethyl)benzenesulfonamide (124)
2,4-dichloro-N-(1H-indol-4-ylmethyl)benzenesulfonamide (125)
3,5-dichloro-N-(1H-indol-4-ylmethyl)benzenesulfonamide (126)
2,6-difluoro-N-(1H-indol-4-ylmethyl)benzenesulfonamide (127)
4-fluoro-N-(1H-indol-4-ylmethyl)-2-methylbenzenesulfonamide (128)
5-fluoro-N-(1H-indol-4-ylmethyl)-2-methylbenzenesulfonamide (129)
N-(1H-indol-4-ylmethyl)thiophene-2-sulfonamide (130)
5-chloro-N-(1H-indol-4-ylmethyl)thiophene-2-sulfonamide (131)
N-(1H-indol-4-ylmethyl)pyridine-3-sulfonamide (132)
N-(1H-indol-4-ylmethyl)quinoline-8-sulfonamide (133)
N-(1H-indol-4-ylmethyl)-2-methylbenzenesulfonamide (134)
N-(1H-indol-4-ylmethyl)-2-(trifluoromethoxy)benzenesulfonamide (135)
2-bromo-N-(1H-indol-4-ylmethyl)benzenesulfonamide (136)
3-bromo-N-(1H-indol-4-ylmethyl)benzenesulfonamide (137)
2,3-dichloro-N-(1H-indol-4-ylmethyl)benzenesulfonamide (138)
2,4,6-trichloro-N-(1H-indol-4-ylmethyl)benzenesulfonamide (139)

FIGS. 4-5 depict the variety of heteroaromatic compounds ($R^3$) that may be used as the heteroaromatic scaffolds for production of N-benzyl-sulfonamides. FIG. 4 provides heteroaromatics where the $R^2$ functional group of FIG. 1 is an aldehyde or carboxaldehyde. FIG. 5 provides heteroaromatics where the $R^2$ functional group is a ketone or a precursor to an aldehyde or a ketone, i.e. the functional group may be an alcohol; a carboxylic acid; an anhydride; an acid chloride, and a dialkylacetal. Indole substrates were found to provide moderate to good yields while carboxaldehydes with indazole and pyrazole cores also efficiently formed N-benzyl sulfonamides. Aldehyde substrates that contain 6-membered N-heteroarenes such as pyridine, quinoline, pyrimidine and pyrazine produced moderate yields of N-benzyl sulfonamides. Finally, thiazole, oxazole and furan based compounds used as N-substrates produced good yields.

Many of the resulting N-benzyl sulfonamides produced by the foregoing method will have pharmacological properties. In particular, many of the compounds will be effective anti-cancer compounds. To determine which compounds will be effective as anti-cancer compounds a new method is needed.

Method of In Vitro Cytotoxicity Screening

In addition to providing the novel method for preparation of N-benzyl sulfonamides, the present disclosure also provides a method for determining the effectiveness of the resulting N-benzyl sulfonamides as pharmacological compounds. Depending on the location of the sulfonamide functionality on the scaffold and the type of sulfonamide functionality, the resulting N-benzyl sulfonamides should have effectiveness in treatment of cancer. The following methods were developed to assess the in vitro effectiveness of the resulting compounds when combined with a metabolic inhibitor.

The N-benzyl sulfonamide library of compounds of FIG. 7 was initially screened for biological activity using a standard cytotoxicity test. The cytotoxicity tests rely upon fluorescence values to determine the cytotoxic impact of the selected compounds on the selected cells. The Table of FIG. 8 demonstrates that compounds 2, 5-9, 11-12, 14, 16, 18-22 were active in cells relative to a control of DMSO. Subsequently, these compounds were tested against the following cancer cell lines obtained from American Type Culture Collection (ATCC), Manassas, VA: $H_{293}$=kidney cancer; BxPC3=pancreatic cancer; HeLa=cervical cancer; MCF7, SkBr3, T47D, MDA-MB=breast cancer; MCF10A=non-cancerous breast; PC3=prostate cancer; NCI-H196=lung cancer. The compounds were also tested against normal cells (HDF).

The cytotoxicity tests were carried out in the following manner. Living cells are known to convert resazurin to the fluorescent compound resorufin. Test systems which rely upon this reaction are commercially available. One such test is known at the Cell Titer Blue Cell Viability test assay from Promega. Cell cultures for each of the identified cancer lines were obtained from ATCC and maintained in Dulbecco's Modified Eagle Medium (DMEM) supplemented with 10% fetal bovine serum (FBS) and pen/strep. As known to those skilled in the art, DMEM typically includes the components identified below.

| Ingredients | mg/L |
|---|---|
| INORGANIC SALTS | |
| Calcium chloride dihydrate | 265.000 |
| Ferric nitrate nonahydrate | 0.100 |
| Magnesium sulphate anhydrous | 97.720 |
| Potassium chloride | 400.000 |
| Sodium chloride | 6400.000 |
| AMINO ACIDS | |
| Glycine | 30.000 |

-continued

| Ingredients | mg/L |
|---|---|
| L-Arginine hydrochloride | 84.000 |
| L-Cystine dihydrochloride | 62.570 |
| L-Glutamine | 584.000 |
| L-Histidine hydrochloride monohydrate | 42.000 |
| L-Isoleucine | 105.000 |
| L-Leucine | 105.000 |
| L-Lysine hydrochloride | 146.000 |
| L-Methionine | 30.000 |
| L-Phenylalanine | 66.000 |
| L-Serine | 42.000 |
| L-Threonine | 95.000 |
| L-Tryptophan | 16.000 |
| L-Tyrosine disodium salt | 103.790 |
| L-Valine | 94.000 |
| VITAMINS | |
| Choline chloride | 4.000 |
| D-Ca-Pantothenate | 4.000 |
| Folic acid | 4.000 |
| Nicotinamide | 4.000 |
| Pyridoxal hydrochloride | 4.000 |
| Riboflavin | 0.400 |
| Thiamine hydrochloride | 4.000 |
| i-Inositol | 7.200 |
| OTHERS | |
| D-Glucose | 4500.000 |
| Phenol red sodium salt | 15.900 |

As known to those skilled in the art, pen/strep is a combination of penicillin and streptomycin used to prevent bacterial and fungal contamination of mammalian cell cultures. The pen/strep solution contains 5,000 Units of Penicillin G (sodium salt) which acts as the active base, and 5,000 micrograms of Streptomycin (sulfate) (base per milliliter), formulated in 0.85% saline.

Figure 8:
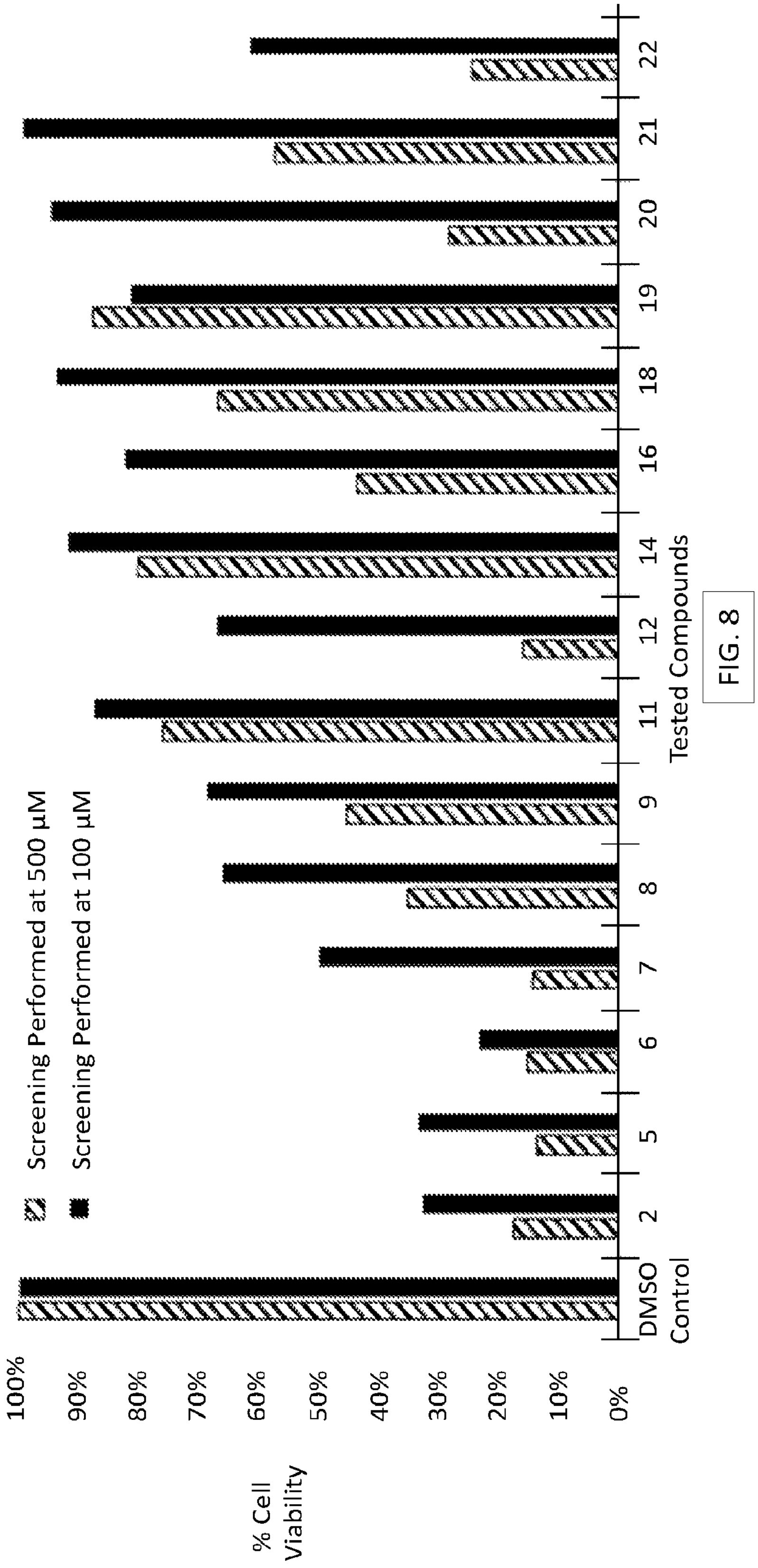
FIG. 8 provides the initial cell viability test results for the screening of compounds 2, 5-9, 11-12, 14, 16, 18-22 of FIG. 7 where each compound was tested at concentrations of 500 μM and 100 μM.

The test method provides for incubating the cell cultures at 37° C. Additionally, the cell cultures are kept under an atmosphere containing 5% $CO_2$. After allowing for proliferation of the cells, the cells were distributed across a plurality of test cells containing from 100 μL DMEM plus 10% FBS and allowed to attach to the surface of the cells. Typically, the time for attachment will require about 12 hours to about 18 hours. Following attachment, the cells were treated with either a solvent control or the N-benzyl sulfonamide compound of interest dissolved in a suitable solvent such as but not limited to DMSO. Typically, about 18 hours to about 36 hours are required to determine the effect of the N-benzyl sulfonamide compound of interest on cell viability. Following treatment of the cells with the N-benzyl sulfonamide or control, the toxicity of the compound to the cells will be determined by addition of 10 μl of CellTiter-Blue reagent, i.e. resazurin. Typically, the resazurin is added between about 18 hours to about 36 hours after treating the cells with the N-benzyl sulfonamides or the control. The cells are allowed to consume and convert the resazurin to resorufin for about one to four hours. Subsequently, the fluorescence of resazurin is measured by excitation at 560 nm and recording the emission at 590 nm within an instrument configured to measure fluorescence intensity. Two commercially available systems are the BioTek Cytation 5 plate reader and the Promega Glomax Multi+detection system. For compounds exhibiting cytotoxicity, the half maximal inhibitory concentration ($IC_{50}$) values were determined using non-linear regression analysis in Graph-Prism software. The method for determining $IC_{50}$ values is well known in the art and will not be discussed further. As known to those skilled in the art, $IC_{50}$ is a quantitative measure that indicates how much of a particular inhibitory substance (e.g. drug) is needed to inhibit, in vitro, a given biological process or biological component by 50%. Therefore, each N-benzyl sulfonamide will be tested over a range of concentrations. Typically, the concentration ranges will be: 6.25 μM, 12.5 μM, 25 μM, 50 μM, and 100 μM. The control in this method is normally dimethyl sulfonamide (DMSO) or other solvent suitable for dissolving the compounds to be tested. FIG. 8 depicts the % cell viability for the indicated compounds depicted in FIG. 7.

Method for Determining ATP Levels Following Treatment with Two Component Compositions The conventional cytotoxicity screening method described above can identify compounds that on their own reduce cell viability; however, the above method will miss biologically active compounds that do not cause cell death. The above method does not provide any information about a compound's biological targets or mechanism of action. Therefore, one aspect of the present invention includes a screening method suitable for identifying compounds which directly inhibit ATP metabolism by select pathways. Additionally, the following method permits identification of the pathway inhibited. Further, the rapid testing method does not require cell death during the exposure of the cells to the compound of interest.

The improved method for identifying such compounds measures ATP levels as a function of light emitted by any ATP dependent luciferase or modified luciferases, i.e. luciferase derivatives. The method uses a conventional luminescent assay to determine the number of viable cells in a culture. The improvement provided by the present method results from pre-treating cells used in the assays with a metabolic inhibitor prior to treatment with the compound of interest. Luminescent assays for determining cytotoxicity are well known in the art. Assays, kits and methods for measuring ATP levels are disclosed by U.S. Pat. Nos. 7,741,067 and 7,083,911, incorporated herein by reference. Commercially available assays, marketed as the CellTiter-Glo® and CellTiter-Blue® from Promega Corporation, are particularly suited for carrying out the method described below; however, other similar luminescent or fluorescent assays will perform equally well in the described method.

The commercially available assays are configured for the purposes of determining cell viability. In normal usage, the test determines ATP levels in untreated cells, i.e. the control. Corresponding cells are treated with an agent of interest that is suspected of reducing cell viability. In the common practice, resulting data is presented as a comparison of the ATP levels in the treated and untreated cells with the decrease in ATP levels indicative of the effectiveness of the agent. The data may be presented as a direct comparison of the assay output levels or as a percentage using the untreated control cells ATP level as 100%.

Figure 13:
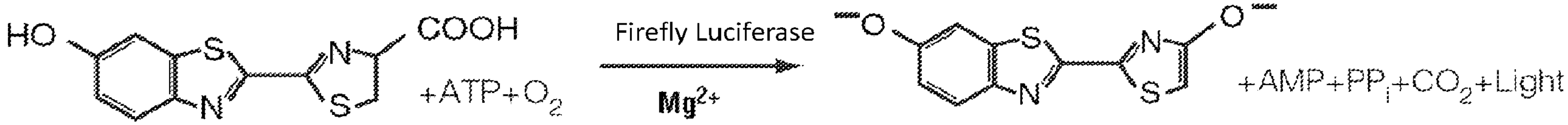
FIG. 13 depicts the light emitting reaction of D-Luciferin in the presence of Firefly Luciferase.

In most instances, following the treatment period, the commercially available assays use a lysis buffer to break the cells apart and release ATP. The releasing agent also contains an enzyme which catalyzes a light emitting reaction. Typically, the enzyme is luciferase and its substrate D-luciferin. In the presence of ATP, luciferase catalyzes a reaction that emits light (see FIG. 13). The resulting light emission corresponds to the ATP levels of the control and the ATP levels of the treated test cells. Thus, the reduction in light intensity emission can be used to determine the level of ATP present in the treated test cells. In most cases, the light emission is quantitated using a photoluminometer. In the conventional testing, if treating cells with a compound reduces cell viability, then their ATP levels will also be reduced (since they are dead they can't make more ATP) relative to the untreated cells. Thus, the traditional CellTiter-Glo assay, commercially available from Promega, method can be described as an indirect measure of cell viability; however, what it really measures is ATP levels, which under certain conditions are indicative of cell viability. These conditions typically involve treating cells for 12-72 hours with compounds of interest, then analyzing using the reagent to produce the light emission.

In the present method, the method of using the available assays has been modified to measure the short-term effect of compounds of interest on ATP levels in the cells. The present method does not result in cell death and does not measure cell viability. In the modified method, the control and test cells are initially treated with the metabolic inhibitor for a period of about thirty minutes to about four hours. Typically, the treatment of the cells with the metabolic inhibitor is for one hour prior to adding the compound to be screened for anti-cancer properties. However, simultaneous treatment with the metabolic inhibitor and the compound being screened should provide satisfactory results. Thus, the modified luminescent assays have been adapted to screen for compounds that directly inhibit ATP metabolism. ATP synthesis in cells occurs over multiple biochemical pathways. These pathways are very responsive to metabolic inhibitors and/or changes in available nutrients. By incorporating a metabolic inhibitor which is known to impact certain pathways, the disclosed method provides for measurement of a compound's direct effects on the remaining metabolic pathways available for ATP synthesis in the cell.

Figure 11:
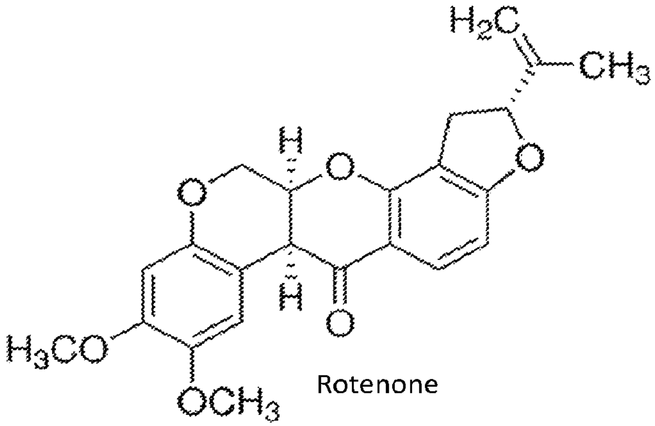
FIG. 11 provides the structure of rotenone.
Figure 12:
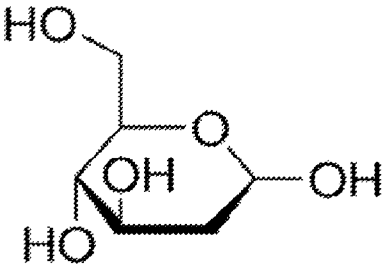
FIG. 12 provides the structure of 2-deoxyglucose.

Because cancers exhibit dysregulation of metabolic pathways, compounds identified in the disclosed method are potential anti-cancer therapeutics. In this screening methodology, cells used in the assays are pretreated with a metabolic inhibitor such as 2-deoxyglucose (2-DG) (inhibits ATP production via glycolysis) or rotenone (inhibits ATP production by mitochondria). As a consequence of the pre-treatment with a metabolic inhibitor, the cell must utilize the remaining uninhibited pathways to maintain cellular ATP levels. FIGS. 11 and 12 provide the structures of rotenone and 2-DG.

Following treatment of the control and test cells with the metabolic inhibitor, the method calls for addition of the compound to be screened for anti-cancer properties to the cells. Following addition of the compound of interest, the assay is allowed to continue for about one hour to about four hours or depending on the luminescing agent up to eighteen hours. However, approximately 60 minutes will be sufficient to determine the ATP inhibiting effect of the compound to be screened on the cells. Following completion of the selected time period, the ATP level within the cell is determined. ATP levels can be determined by luminescence according to standard measuring procedures, i.e. the luminescence level of the assay from the living cells treated with the two component composition is compared to the luminescence level of the assay from the living cells without the two component composition, i.e., the control experiment. Thus, the ATP levels are determined without killing the cells during the incubation of the cells in the presence of the compound of interest. As a result, the measured reduction in ATP level corresponds directly to the inhibition of the metabolic pathways uninhibited by the metabolic blocker.

Thus, the method provides the ability to screen compounds for the ability to specifically target the uninhibited pathway being used to generate ATP. Furthermore, because cells pre-treated with a metabolic inhibitor targeting a first known pathway are forced to use an alternative known pathway that is not inhibited to maintain ATP levels, the screening method provides immediate mechanistic information about the active compound mechanism of action. These results are provided in a relatively short time period of about ninety minutes to about five hours.

A wide variety of ATP luminescing detection reagents are available commercially. So long as the reagent produces a luminescence in the presence of ATP, the reagent will be suitable for use in the present method. Suitable reagents include but are not limited to any ATP dependent luciferase such as but not limited to firefly luciferase, other modified luciferase based reagents, i.e. luciferase derivatives. According to the rapid method for determining the anti-cancer activity of a compound, a sample of living cells is distributed across a number of testing wells. Typically, 96-well plates are used; however, the number of wells is not critical to the current method. When using a 96-well plate the number of living cells will commonly be about 20,000. The sample wells contain a cell growth medium to promote cell health and growth and an additive to prevent bacterial contamination of the wells. One common example of the cell growth medium is DMEM with 10% FBS as described above. One example of the additive to prevent bacterial contamination is a solution of penicillin G and streptomycin referred to commonly as Pen-Strep. The Pen-Strep solution typically contains 5000 units of penicillin G and 5000 micrograms of streptomycin. Thus, the rapid determination of anti-cancer compounds can be carried out using the following method.

- The desired number of cells are distributed in a 96-well plate containing 100 μL DMEM plus 10% FBS with optional Pen-Strep.
- After 24 hours, cells are treated with the compound of interest or a 5% solution of dimethyl sulfoxide (DMSO) in water as a control.
- The time period for exposure to the compound of interest and the DMSO control will vary depending on the luminescing detection reagent. However, when using a commercially available reagent such as resazurin (CellTiter Blue commercially available from Promega) or luciferase or a luciferase derivative (CellTiter Glo commercially available from Promega) the time period can be readily determined with reference to literature from the commercial source. Other luminescing detection agents can also be used with minimal experimentation to determine the desired compound exposure time.
- Upon completion of the time period for exposure to the compound of interest or the DMSO, 10 μL of the luminescing detection reagent is added and the cells are lysed by a detergent added along with the luminescing detection reagent.
  - When the reagent is resazurin, as found in CellTiter-Blue the time period for exposure to the compound of interest and the DMSO will be about 24 hours.
  - When the reagent is luciferase or a luciferase derivative as found in CellTiter-Glo the time period for exposure to the compound of interest and the DMSO will be about 30 minutes to four hours.
- The luminescing detection reagent is added over a period of time.
  - When using resazurin, the time period for the addition of the 10 μl volume takes place over a period of about one to four hours.
  - When using luciferase or a luciferase derivative, the time period is about 3 minutes to about 7 minutes, typically about 5 minutes.
- During the time period of addition of the luminescing detection reagent the resulting luminescence is measured using conventional methods and devices. Suitable devices for measuring luminescence include but are not limited to a luminometer, a luminescence microplate reader or other devices with a photomultiplier tube.
- The impact of the compound of interest on the cell is determined by a reduction in luminescence. If the compound of interest deactivates the cell, then the cell produces less or no ATP. As a result, the cells in the well treated with the compound of interest will have a lower luminescence value as compared to the cells in wells treated with DMSO.
- The value for the cells treated with the compound of interest is reported as a "percent of control" (POC) value. The determination of POC is calculated by dividing the averaged response from duplicate wells containing the cells as treated with the compound of interest by the average response of duplicate control wells which contain only cells and DMSO (in other words, a blank control experiment).

Table 1 reports the POC values for a variety of compounds of interest. The number in the far left column of Table 1 corresponds to the compound number of compounds depicted in FIGS. 7A-7C. Each compound was tested according to the above described method. Additionally, each compound was tested in combination with a metabolic inhibitor. When using the metabolic inhibitor, the metabolic inhibitor may be added prior to the compound of interest or simultaneously with the compound of interest. To provide the best results when seeking to determine the metabolic pathway impacted by the compound of interest, the metabolic inhibitor should be added for a period of about thirty minutes to about four hours prior to the addition of the compound of interest.

As reported in Table 1 below, one group of assays included only the compound of interest. Another group of assays included the compound of interest in combination with 2-deoxyglucose and a third group of assays included the compound of interest with rotenone. Other metabolic inhibitors suitable for use in the disclosed method include but are not limited to: 2-deoxyglucose, rotenone, Lonidamine, 3-bromopyruvate, imatinib, oxythiamine, and 6-aminonicotinamide Glutaminase Inhibitor 968, 6-Diazo-5-oxo-L-norleucine, Amytal, Antimycin A, Sodium Azide, Cyanides, oligomycin, FCCP, Phloretin, Quercetin, 3BP, 3PO, DCA, NHI-1 and Oxamic acid, Fisetin, myricetin, apigenin, genistein, cyanidin, daidzein, hesperetin, naringenin, and catechin.

- For assays that included 2-deoxyglucose (2-DG), a 1M aqueous stock solution was prepared. In carrying out the analysis, 1-2 μL of the 1M 2-DG was added directly to the well containing 100 μL of cells, DMEM and 10% FBS. The resulting dilution of the 2-DG provides a concentration of 2-DG at about 10-20 mM in the well. The compound of interest is added as a 100 μM solution to the well.
- For assays that include rotenone, a 30 mM stock solution of rotenone in DMSO is prepared and diluted with water to provide a final 125 μM concentration of rotenone. In carrying out the analysis, 1 μL of this stock rotenone solution is added to the well containing 100 μL of cells, DMEM and 10% FBS. The resulting dilution of the rotenone stock solution provides a rotenone concentration of approximately 1.25 μM in the well. The compound of interest is added as a 100 μM solution to the well.

In Table 1 below, the cell lines tested are reported across the top row of the table. The POC values are reported for each compound of interest and each combination of interest in combination with 2DG or rotenone. A POC value of less than 50 reflects the likely inhibition of the cell line by the compound of interest or the combination of the compound of interest with the indicated metabolic inhibitor. Compound 2 in particular demonstrated reduction in luminescence, corresponding to reduced ATP activity by the cells, across many of the cell lines. When combined with 2-DG compound, 2 showed effectiveness against each cell line and a remarkable value for BxPC3 the pancreatic cancer cell line. Compound 2 would also be expected to have effectiveness against other pancreatic cancer cell lines.

Synergistic Composition for Treatment of Cancer

While the resulting N-benzyl sulfonamides provided by the method discussed above have shown some effectiveness in vitro against select cancer cell lines, further toxicity against cancer cells would be desired. To that end, the present disclosure also provides a two-component composition which has shown a synergistic effect against cancer cells in vitro.

The two-component composition consists of a N-benzyl sulfonamide and a metabolic inhibitor. In one embodiment, the metabolic inhibitor is 2-deoxyglucose (2-DG). In another embodiment, the metabolic inhibitor is rotenone. Other metabolic inhibitors suitable for use in the two-component composition are: Lonidamine, 3-bromopyruvate, imatinib, oxythiamine, and 6-aminonicotinamide Glutaminase Inhibitor 968, 6-Diazo-5-oxo-L-norleucine, Amytal, Antimycin A, Sodium Azide, Cyanides, oligomycin, FCCP, Phloretin, Quercetin, 3BP, 3PO, DCA, NHI-1 and Oxamic acid, Fisetin, myricetin, apigenin, genistein, cyanidin, daidzein, hesperetin, naringenin, and catechin. While subsequent in vivo testing may determine a narrower range for the ratio of the N-benzyl sulfonamide to the metabolic inhibitor, the current ratio that has demonstrated effectiveness against cancer lines, as identified in the table below, is in the range of about 1:50 to about 1:1500. Thus, the metabolic inhibitor may comprise from about 75% by weight to about 99.99% by weight of the composition containing both N-benzyl sulfonamide to the metabolic inhibitor where the N-benzyl sulfonamide has the structure set forth in FIG. 14. Thus, the two part composition may be effective with as little as about 0.001% by weight N-benzyl sulfonamide up to about 25% by weight.

Figure 10:
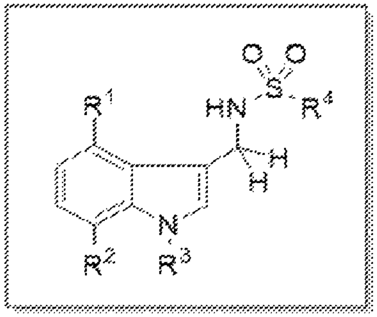
FIG. 10 provides the $IC_{50}$ results for the indicated compounds from FIGS. 7-9 prepared according to the disclosed method for determining ATP levels following treatment with two component compositions compared to two known anti-cancer compounds ABT-751 and Indisulam.

The Table of FIG. 9 provides the results of cytotoxicity testing a 100 μM concentration of compounds 2, 5-9, 11-12, 14, 16, 18-22 of FIG. 7 against the indicated cancer cell lines using CellTiter-Blue assay with 24 hour compound incubation time. FIG. 9 reflects the percent reduction in cell viability resulting from the treatment of the indicated cancer cell lines with the indicated compounds. As indicated by the boxed values in FIG. 9, compounds 2, 5, and 6 would be considered effective against H293. Additionally, compound 5 displayed effectiveness against HeLa, NCI-H196, MCF10A. Thus, some degree of effectiveness against cancer cell lines was demonstrated. The Table of FIG. 10 provides a comparison of the $IC_{50}$ values of select compounds from FIG. 7 to the $IC_{50}$ values of two known anti-cancer sulfonamides, ABT-751 and Indisulam. As indicated by FIG. 10, the identified compounds performed remarkably better than the known anti-cancer agents. Thus, the identified compounds are expected to have greater anti-cancer potency.

Table 1 below provides the results of testing 30 different N-benzyl sulfonamides, as depicted in FIG. 7, alone and in combination with metabolic inhibitors. The tests were carried out using the method for determining ATP levels using CellTiter-Glo reagent according to the improved method using a two hour incubation following treatment with two component compositions described in the previous section. In the following table, values less than 50% (bold and underlined) of the control value, as generated using the solvent DMSO, generally reflect effectiveness against the indicated cancer cell line. Additionally, the results reported in the table demonstrate the generally synergistic effect of the two-component composition against the tested cancer cell lines.

While the two-component composition of N-benzyl sulfonamide with rotenone showed effectiveness against several cell lines, the combination of 100 μM N-benzyl sulfonamide compound number 2 as identified in FIG. 7 with 10 Mm 2-DG demonstrated remarkable effectiveness against every cancer cell line tested. In particular, this combination showed effectiveness against the very difficult to treat pancreatic cell line. See the second row of the table below and the column identified as BxPC3. Of additional significance are compounds (such as 1, 3, 4, 22, and 23) that had little effect on the majority of cell lines, but had significant effect against the pancreatic cancer cell line BxPC3. This display of selectivity in the presence of 2-DG is significant, because it indicates compounds identified in the modified screening methodology can be combined with known drugs to specifically target and kill cancer cells. It is important to note that compounds identified using this screening methodology would have been completely missed using more traditional approaches.

TABLE 1

| All 100 uM | HDF | H293 | BxPC3 | HeLa | MCF7 | MCF10A | MDA-MB | NCI-H196 | PC3 | SkBr3 | T47D |
|---|---|---|---|---|---|---|---|---|---|---|---|
| 1 | 98.5 | 92.8 | 97.1 | 95 | 102.7 | 73.3 | 78.1 | 90.8 | 91.7 | 97.7 | 53.2 |
| 1 + 2DG | 85 | **48.2** | **27.4** | 66.3 | 86.8 | 86.7 | 62 | 68.8 | 57.3 | 72.9 | **43.2** |
| 1 + rotenone | 107.7 | 69 | 86.6 | 78.7 | 79.6 | 69 | 80.5 | 83.2 | 72.6 | 91.2 | 76.6 |
| 2 | **49.3** | **43.8** | 69 | 64.6 | 70.1 | **42.9** | **48.1** | 50.9 | **30.9** | 72.6 | **22.2** |
| 2 + 2DG | **37.5** | **20** | **13.7** | **30.8** | **25.1** | **23.7** | **37.8** | **22.9** | **16.7** | **38** | **16.6** |
| 2 + rotenone | 57.6 | **47.6** | 86.4 | 57.5 | 56.9 | 58.7 | 55.7 | **23.5** | **36.6** | 72.6 | **30.8** |
| 3 | 84.5 | 74.3 | 96.8 | 99.2 | 104.8 | 62.5 | 92.4 | 89.6 | 85 | 72.8 | **34.9** |
| 3 + 2DG | 72.7 | **42.8** | **26.1** | 67.6 | 74.5 | 72.7 | 81.8 | 55 | 59.4 | 79.4 | **37.1** |
| 3 + rotenone | 91.9 | 69.3 | 84.5 | 85.5 | 97.3 | 110.5 | 102.7 | 89.2 | 65.1 | 97.1 | 58.7 |
| 4 | 88.1 | 88.6 | 88.4 | 90.6 | 108.3 | 59.7 | 94.7 | 72.5 | 93.7 | 79.1 | **48.9** |
| 4 + 2DG | 66.8 | 60 | **21.2** | 67.4 | 82.2 | 84.8 | 63.6 | **49.6** | 61.9 | 87.5 | **36.3** |
| 4 + rotenone | 88.6 | 65.8 | 71.1 | 84.3 | 79.2 | 89.8 | 71.9 | 61.5 | 61.3 | 96.8 | **45.8** |
| 5 | 70.5 | **49.7** | 54.3 | 76.1 | 86.4 | 55.3 | 54.4 | **47.7** | 68.3 | 71.1 | **36.6** |
| 5 + 2DG | **16.1** | **17.2** | **10.5** | **22.3** | **18.7** | **15.8** | **24.7** | **4.2** | **4.8** | **37.1** | **13.8** |
| 5 + rotenone | 83.5 | **41.2** | **36.5** | **31.9** | 55.6 | **45** | **24.6** | **9.1** | **18.3** | 60 | **36** |

TABLE 1-continued

| All 100 uM | HDF | H293 | BxPC3 | HeLa | MCF7 | MCF10A | MDA-MB | NCI-H196 | PC3 | SkBr3 | T47D |
|---|---|---|---|---|---|---|---|---|---|---|---|
| 6 | **48.8** | 62.6 | 68.9 | 75.3 | 72 | 52.3 | 57.2 | 64.3 | **38.3** | 97 | **23.7** |
| 6 + 2DG | **37.7** | **31.6** | **33.4** | **47.3** | **41** | **41.3** | 58.5 | **34.3** | **35.9** | 55.9 | **19.7** |
| 6 + rotenone | 61.3 | **49.6** | 69.7 | 66.9 | 63.4 | 87.8 | 67.3 | **23.7** | 54.3 | 79.4 | **39.1** |
| 7 | 87.7 | 93.2 | 86.3 | 91 | 107.4 | 66 | 85.6 | 84.9 | 95 | 108.5 | **46.5** |
| 7 + 2DG | 60.8 | 60.9 | 60.9 | 70.6 | 91.6 | 64.5 | 81.2 | 70.1 | 59.4 | 76.2 | **40.1** |
| 7 + rotenone | 77.9 | 65.3 | 79.1 | 79.5 | 75.9 | 97.9 | 102.4 | 77.7 | 82 | 88.2 | 66 |
| 8 | 99 | 111.6 | 106.3 | 105.6 | 140.3 | 94.6 | 93.9 | 91.1 | 109.3 | 88.8 | 64.1 |
| 8 + 2DG | 91.3 | 83.5 | 87.1 | 80.8 | 86.2 | 77.9 | 91.7 | 99.2 | 87.9 | 97.1 | 94.6 |
| 8 + rotenone | 88.3 | 87.1 | 93.5 | 99.1 | 116.7 | 94.4 | 86.2 | 95.1 | 108.3 | 103.7 | 101.2 |
| 9 | 86.4 | 83.3 | 114.5 | 97.3 | 117.2 | 89.6 | 95.6 | 93.1 | 90.4 | 74.1 | 50.3 |
| 9 + 2DG | 88.5 | 76.6 | 57.6 | 80.5 | 75.8 | 88.3 | 91.7 | 86.1 | 89.3 | 89.9 | 58.9 |
| 9 + rotenone | 107.6 | 88.5 | 118.5 | 89.8 | 95.1 | 123.7 | 114 | 117.7 | 101.7 | 115.5 | 103.5 |
| 10 | 88.6 | 105.6 | 66.3 | 106.3 | 115 | 92 | 94.1 | 105.5 | 115.3 | 90.8 | 63.5 |
| 10 + 2DG | 92.7 | 84 | 62.9 | 91.3 | 121.2 | 100.4 | 86.7 | 90.8 | 97.8 | 98 | 76.6 |
| 10 + rotenone | 82.2 | 70.8 | 54.4 | 85.5 | 89.4 | 83.5 | 87.4 | 103.7 | 98.7 | 107.3 | 91.4 |
| 11 | 77.4 | 92.8 | 99.2 | 103.1 | 117.7 | 95.4 | 95.3 | 95.2 | 113.4 | 100.8 | 59.3 |
| 11 + 2DG | 101.3 | 87.4 | 83.8 | 117.6 | 98.4 | 95.8 | 82.4 | 114.7 | 94.6 | 99.7 | 90.4 |
| 11 + rotenone | 89.8 | 88.3 | 78 | 96.4 | 94.6 | 93.7 | 97.9 | 88.9 | 96.1 | 95.3 | 99.6 |
| 12 | 77.8 | 94.4 | 79.8 | 98 | 97.3 | 98.6 | 87.2 | 83.5 | 82.1 | 91.6 | 59.8 |
| 12 + 2DG | 90.9 | 85 | 57 | 78.5 | 90.8 | 88.1 | 83.9 | 117 | 89.9 | 73.5 | 58.1 |
| 12 + rotenone | 70.4 | 74.9 | 61 | 87.6 | 92.1 | 86.1 | 105.7 | 81.8 | 80.3 | 85.1 | 95.2 |
| 13 | 96.5 | 101.1 | 91.2 | 94.6 | 126.7 | 94.8 | 101.1 | 87.6 | 82.2 | 101.1 | 84.3 |
| 13 + 2DG | 104.2 | 69.4 | 74.1 | 90.7 | 89.7 | 96.1 | 81.9 | 127.4 | 97.3 | 87.2 | 88.8 |
| 13 + rotenone | 98.3 | 81.1 | 55.3 | 94.1 | 116.5 | 84 | 103.8 | 99.7 | 101.2 | 96.5 | 90 |
| 14 | 96.1 | 84.9 | 93.8 | 98.3 | 125.8 | 102.9 | 105.2 | 86.9 | 110.9 | 107.1 | 86.7 |
| 14 + 2DG | 96.3 | 82.1 | 95.4 | 106.4 | 109.8 | 119.1 | 86 | 107.3 | 101.7 | 96.9 | 106.4 |
| 14 + rotenone | 90.9 | 82.4 | 60.9 | 102.1 | 94.4 | 94.3 | 87.5 | 109 | 101.7 | 98.3 | 114.8 |
| 15 | 89.2 | 99.8 | 98.8 | 102.8 | 148 | 105.2 | 108.4 | 92.3 | 109 | 116.6 | 89.6 |
| 15 + 2DG | 100.2 | 74.7 | 70.8 | 113.9 | 103.4 | 122 | 91.2 | 115.4 | 117.6 | 123.3 | 82.5 |
| 15 + rotenone | 91.1 | 84.4 | 88.9 | 102.2 | 96.4 | 98.4 | 90.8 | 104.5 | 106.4 | 93 | 109.4 |
| 16 | 94.3 | 80.1 | 103 | 96.8 | 123.4 | 113.1 | 105.5 | 110.5 | 108.8 | 91.9 | 91.1 |
| 16 + 2DG | 95.6 | 80.7 | 95.4 | 106.8 | 93.3 | 118.9 | 104.5 | 99.2 | 113.1 | 81.4 | 111.6 |
| 16 + rotenone | 98.3 | 81.6 | 72.7 | 102.3 | 107.5 | 86.2 | 92.7 | 97.6 | 95.1 | 104 | 99.3 |
| 17 | 90.7 | 80.4 | 91.4 | 90.3 | 145.3 | 92.4 | 104.8 | 96.8 | 112.8 | 90.1 | 83 |
| 17 + 2DG | 98 | 85.8 | 101.4 | 118.8 | 114.6 | 97.1 | 89.8 | 103.8 | 93.7 | 88.8 | 89.1 |
| 17 + rotenone | 84.1 | 74.9 | 75.7 | 110.3 | 90.6 | 91.6 | 98.1 | 89.4 | 90.9 | 95.4 | 104.6 |
| 18 | 96.1 | 67.3 | 100.2 | 99.5 | 109.8 | 118.6 | 102.2 | 97.4 | 74 | 112.5 | 95.7 |
| 18 + 2DG | 93 | 96.3 | 85.4 | 100 | 137.3 | 92.2 | 86.1 | 108.3 | 94 | 107.2 | 82.8 |
| 18 + rotenone | 95.7 | 67.4 | 94.3 | 97.3 | 82 | 86.9 | 100 | 87.3 | 97.2 | 96.6 | 100.6 |
| 19 | 92.5 | 82.2 | 96.2 | 104 | 133.5 | 83.9 | 104.1 | 117.2 | 108 | 119.2 | 91.5 |
| 19 + 2DG | 98.9 | 87.2 | 98.4 | 94.8 | 104 | 95.8 | 89.5 | 107.3 | 127.1 | 105.9 | 87.4 |
| 19 + rotenone | 87.3 | 79.1 | 107.2 | 109.3 | 92.1 | 119.8 | 112 | 94.3 | 98.9 | 108.6 | 86.7 |
| 20 | 90.9 | 104.1 | 95.8 | 103.2 | 138.5 | 101.6 | 97.4 | 100.4 | 91.1 | 103.5 | 73.9 |
| 20 + 2DG | 88.1 | 84.4 | 86.4 | 91.7 | 87.3 | 78.1 | 82.9 | 90.6 | 83.8 | 96.7 | 69.7 |
| 20 + rotenone | 103.1 | 69.4 | 94.8 | 117.2 | 124.6 | 102.9 | 98.5 | 102.1 | 100.4 | 102.5 | 101.6 |
| 21 | 87.9 | 115.1 | 112.4 | 100.8 | 189.4 | 108.1 | 101 | 107.9 | 93.3 | 102 | 88.7 |
| 21 + 2DG | 97.4 | 87.8 | 106.8 | 105.8 | 121.1 | 92.8 | 100.7 | 107.4 | 131.7 | 108.5 | 99.4 |
| 21 + rotenone | 113.6 | 87 | 114.8 | 109.4 | 111 | 120 | 121.5 | 130.5 | 110.9 | 106.9 | 86.4 |
| 22 | 89.7 | 121.9 | 99.1 | 100.8 | 113.1 | 104.9 | 96.7 | 116.8 | 93 | 106 | 85.3 |
| 22 + 2DG | 76.3 | 69.9 | **42.9** | 94.5 | 107.1 | 70.2 | 86.5 | 94.6 | 94.5 | 83.5 | 62.5 |
| 22 + rotenone | 85.5 | 90.9 | 70.8 | 105.2 | 96.4 | 96.9 | 87.1 | 94.2 | 108.2 | 93.5 | 109.3 |
| 23 | 74.6 | 92.1 | 95.9 | 84.1 | 96.3 | 85 | 98.6 | 93 | 77.3 | 85.9 | 54 |
| 23 + 2DG | 90.6 | **47.4** | **34.9** | 86.9 | 93.6 | 82.8 | 85.9 | 83.5 | 92.9 | 75.5 | **46.6** |
| 23 + rotenone | 119.9 | 65.3 | 78.5 | 93.7 | 121.1 | 85.1 | 83 | 85.6 | 87.9 | 87.7 | 71.7 |
| 24 | 57.2 | 62.6 | 59 | 78.9 | 82.9 | 85.1 | 96.4 | 172 | 54.6 | 93.4 | 70.6 |
| 24 + 2DG | 65.6 | **42.1** | **43.1** | 80.4 | 55.7 | 56.8 | **41.5** | 54.6 | 52.5 | 66.5 | **49.7** |
| 24 + rotenone | 95.7 | **47.6** | **38.6** | 96.1 | 66.5 | 59.1 | **49.7** | 73.3 | **47.5** | 67.2 | 65.5 |
| 25 | 79.2 | 99.7 | 85.1 | 89.4 | 112.2 | 95.7 | 103 | 305 | 60.2 | 112.5 | 94.4 |
| 25 + 2DG | 93.6 | 79.6 | 71.5 | 90.8 | 92.9 | 98.3 | 86.2 | 92.9 | 96.8 | 88.2 | 88.9 |
| 25 + rotenone | 95.5 | 68.8 | 78.2 | 95.6 | 104.2 | 80.4 | 88.8 | 83 | 80.1 | 104.1 | 86.7 |
| 26 | 106.1 | 109.7 | 99.1 | 90.4 | 113.6 | 106 | 90.2 | 220 | 92.3 | 108.9 | 93.3 |
| 26 + 2DG | 91.1 | 72.9 | 86.6 | 106.9 | 95.9 | 99.9 | 87.6 | 91.3 | 111.5 | 95.7 | 101 |
| 26 + rotenone | 86.9 | 72 | 88.8 | 96.3 | 119.8 | 81 | 79.2 | 80.8 | 89.6 | 97.1 | 90.8 |
| 27 | 65 | 67 | **42.8** | 58.3 | 82.9 | 58.9 | 62.6 | 150 | **43.1** | 95.6 | **33.9** |
| 27 + 2DG | **38** | **30.4** | **14.2** | 104.3 | 50.2 | **27.1** | **27.3** | 117.2 | **15.2** | 62.4 | 103.1 |
| 27 + rotenone | 66.6 | **27.3** | **15.8** | 73.3 | 61.1 | **30.2** | **37.3** | **16.7** | **27.2** | 66 | 103.8 |
| 28 | 74.9 | **43.2** | **40.4** | 57.7 | 79 | 72.8 | 77.4 | 129 | **31.8** | 102.3 | 66.1 |
| 28 + 2DG | 56.1 | **49** | **41.8** | 65.6 | 60.7 | **29.5** | **45.5** | **40.4** | 56.5 | 79.6 | **33.7** |
| 28 + rotenone | 62.2 | **43.3** | **44.6** | 96.1 | 53.5 | 81.1 | 78.1 | 60.6 | 64.8 | 87.3 | 62.2 |
| 29 | 95.8 | 91.2 | 80.8 | 80.9 | 104.7 | 78.9 | 81.1 | 192 | 77.8 | 102.3 | 90 |
| 29 + 2DG | 73 | 55 | 51.7 | 83.9 | 90.9 | **46.2** | 64.7 | 51.3 | 67.5 | 72.5 | 60.7 |
| 29 + rotenone | 81.5 | 50.5 | 52.7 | 93.1 | 98 | 62.7 | 69.7 | 100.3 | 67 | 78.6 | 77.6 |
| 30 | **28.2** | **14** | **15.8** | **28.5** | **37.4** | **30** | **38.6** | **48** | **7.1** | 64.1 | **16.1** |
| 30 + 2DG | **28.4** | **12.8** | **6.3** | **17.8** | **11.3** | **8.4** | **41.5** | **18.7** | **10.6** | **41.3** | **13.2** |
| 30 + rotenone | 66.2 | **9.5** | **45.7** | 58.4 | **36** | **34.6** | **48.3** | **18.4** | **21.7** | 58.2 | **28** |

Other embodiments of the present invention will be apparent to one skilled in the art. As such, the foregoing description merely enables and describes the general uses and methods of the present invention. Accordingly, the following claims define the true scope of the present invention.

What is claimed is:

1. A method for determining the cytotoxicity of a compound of interest, the method comprising:

providing a first sample of living cells in a first test well;

providing a second sample of living cells in a second test well;

adding a metabolic inhibitor to said first sample of living cells;

adding the same metabolic inhibitor to the second sample of living cells;

less than four hours after addition of the metabolic inhibitor to the first sample of living cells, treating the first sample of living cells with the compound of interest;

less than four hours after addition of the metabolic inhibitor to the first sample of living cells, treating the second sample of living cells with a suitable control compound;

selecting a luminescing detection agent and determining the time period for exposure of the first sample of living cells to the compound of interest which must pass prior to addition of the selected luminescing detection agent to said first sample of living cells and said second sample of living cells based on the selected luminescing detection agent;

adding the luminescing detection agent to said first sample of living cells over a period of time as determined by the selected luminescing detection agent and adding said luminescing detection agent to said second sample of living cells over a period of time as determined by the selected luminescing detection agent;

measuring the resulting luminescence produced by the first sample of living cells;

measuring the resulting luminescence produced by the second sample of living cells;

the difference between the luminescence of the first sample of living cells and the luminescence of the second sample of living cells reflects a reduction in ATP levels in the first sample of living cells which is indicative of the cytotoxicity of the compound of interest; and, said step of treating the first sample of living cells with the compound of interest does not result in cell death.

2. The method of claim 1, further comprising the step of adding a metabolic inhibitor to said first sample of living cells and to the second sample of living cells.

3. The method of claim 2 further comprising the step of determining the metabolic pathway affected by the compound of interest based on the selected metabolic inhibitor.

4. The method of claim 1 wherein said compound of interest is a N-benzyl sulfonamide having an indole heteroaromatic group.

5. The method of claim 2 wherein said metabolic inhibitor is selected from the group consisting of 2-deoxyglucose, rotenone, Lonidamine, 3-bromopyruvate, imatinib, oxythiamine, and 6-aminonicotinamide Glutaminase Inhibitor 968, 6-Diazo-5-oxo-L-norleucine, Amytal, Antimycin A, Sodium Azide, Cyanides, oligomycin, FCCP, Phloretin, Quercetin, 3BP, 3PO, DCA, NHI-1 and Oxamic acid, Fisetin, myricetin, apigenin, genistein, cyanidin, daidzein, hesperetin, naringenin, and catechin.

6. The method of claim 1 wherein said first sample of living cells and said second sample of living cells is a pancreatic cancer cell line.

7. The method of claim 1 wherein said suitable control compound is any solvent suitable for dissolving the compound of interest.

8. The method of claim 1 wherein said suitable luminescing detection agent is selected from the group of ATP dependent luciferases and luciferase derivatives.

9. The method of claim 1 wherein said suitable luminescing detection agent is resazurin and wherein the time period for exposure of the first sample of living cells to the compound of interest and the time period for exposure to the suitable control compound is about 24 hours and wherein the period of time for adding the resazurin to the first sample of living cells is about one hour to about four hours and wherein the period of time for adding the resazurin to the second sample of living cells is about one hour to about four hours.

10. The method of claim 1 wherein said suitable luminescing detection agent is luciferase or a luciferase derivative and wherein the time period for exposure of the first sample of living cells to the compound of interest and the time period for exposure to the suitable control compound is about 30 minutes to about four hours and wherein the period of time for adding the luciferase or a luciferase derivative to the first sample of living cells is about 3 minutes to about 7 minutes and wherein the period of time for adding the luciferase or a luciferase derivative to the second sample of living cells is about 3 minutes to about 7 minutes.

11. A method for determining the cytotoxicity of a compound of interest, the method comprising:

providing a first sample of living cells in a first test well;

providing a second sample of living cells in a second test well;

adding a metabolic inhibitor to the first sample of living cells and to the second sample of living cells, simultaneous with the step of adding the metabolic inhibitor, treating the first sample of living cells with the compound of interest;

simultaneous with the step of adding the metabolic inhibitor, treating the second sample of living cells with a suitable control compound;

selecting a luminescing detection agent and determining the time period for exposure of the first sample of living cells to the compound of interest which must pass prior to addition of the selected luminescing detection agent to said first sample of living cells and said second sample of living cells based on the selected luminescing detection agent;

adding the luminescing detection agent to said first sample of living cells over a period of time as determined by the selected luminescing detection agent and adding said luminescing detection agent to said second sample of living cells over a period of time as determined by the selected luminescing detection agent;

measuring the resulting luminescence produced by the first sample of living cells;

measuring the resulting luminescence produced by the second sample of living cells;

the difference between the luminescence of the first sample of living cells and the luminescence of the second sample of living cells reflects a reduction in ATP levels in the first sample of living cells which is indicative of the cytotoxicity of the compound of interest; and, said step of treating the first sample of living cells with the compound of interest does not result in cell death.

12. The method of claim 11, further comprising the step of determining the metabolic pathway affected by the compound of interest based on the selected metabolic inhibitor.

13. The method of claim 11, wherein said metabolic inhibitor is selected from the group consisting of 2-deoxyglucose, rotenone, Lonidamine, 3-bromopyruvate, imatinib, oxythiamine, and 6-aminonicotinamide Glutaminase Inhibitor 968, 6-Diazo-5-oxo-L-norleucine, Amytal, Antimycin A, Sodium Azide, Cyanides, oligomycin, FCCP, Phloretin, Quercetin, 3BP, 3PO, DCA, NHI-1 and Oxamic acid, Fisetin, myricetin, apigenin, genistein, cyanidin, daidzein, hesperetin, naringenin, and catechin.

14. A method for determining the cytotoxicity of a compound of interest, the method comprising:

providing a first sample of living cells in a first test well;

providing a second sample of living cells in a second test well;

adding a metabolic inhibitor to said first sample of living cells;

adding the same metabolic inhibitor to the second sample of living cells;

treating the first sample of living cells with the compound of interest;

treating the second sample of living cells with a suitable control compound;

selecting a luminescing detection agent and determining the time period for exposure of the first sample of living cells to the compound of interest which must pass prior to addition of the selected luminescing detection agent to said first sample of living cells and said second sample of living cells based on the selected luminescing detection agent;

adding the luminescing detection agent to said first sample of living cells over a period of time as determined by the selected luminescing detection agent and adding said luminescing detection agent to said second sample of living cells over a period of time as determined by the selected luminescing detection agent;

measuring the resulting luminescence produced by the first sample of living cells;

measuring the resulting luminescence produced by the second sample of living cells;

the difference between the luminescence of the first sample of living cells and the luminescence of the second sample of living cells reflects a reduction in ATP levels in the first sample of living cells which is indicative of the cytotoxicity of the compound of interest;

said step of treating the first sample of living cells with the compound of interest does not result in cell death; and, determining the metabolic pathway affected by the compound of interest based on the selected metabolic inhibitor.

15. The method of claim 14, wherein said metabolic inhibitor is selected from the group consisting of 2-deoxyglucose, rotenone, Lonidamine, 3-bromopyruvate, imatinib, oxythiamine, and 6-aminonicotinamide Glutaminase Inhibitor 968, 6-Diazo-5-oxo-L-norleucine, Amytal, Antimycin A, Sodium Azide, Cyanides, oligomycin, FCCP, Phloretin, Quercetin, 3BP, 3PO, DCA, NHI-1 and Oxamic acid, Fisetin, myricetin, apigenin, genistein, cyanidin, daidzein, hesperetin, naringenin, and catechin.

16. The method of claim 14, wherein said step of adding the metabolic inhibitor to said first sample of living cells takes place prior to the addition of the compound of interest and said step of adding said compound of interest to said first sample of living cells takes place about 30 minutes to about four hours after the addition of the metabolic inhibitor and said step of adding the suitable control compound takes place about 30 minutes to about four hours after the addition of the metabolic inhibitor.

17. The method of claim 14, wherein the step of adding the metabolic inhibitor takes place simultaneously with the addition of the compound of interest and the suitable control compound.

* * * * *